US006846653B2

(12) United States Patent
Kolkman

(10) Patent No.: US 6,846,653 B2
(45) Date of Patent: Jan. 25, 2005

(54) ENHANCED SECRETION OF A POLYPEPTIDE BY A MICROORGANISM

(75) Inventor: Marc Kolkman, Oegstgeest (NL)

(73) Assignee: Genencor International, Inc., Palo Alto, CA (US)

( * ) Notice: Subject to any disclaimer, the term of this patent is extended or adjusted under 35 U.S.C. 154(b) by 147 days.

(21) Appl. No.: 09/975,132

(22) Filed: Oct. 9, 2001

(65) Prior Publication Data

US 2002/0182672 A1 Dec. 5, 2002

Related U.S. Application Data

(60) Provisional application No. 60/239,531, filed on Oct. 10, 2000.

(51) Int. Cl.[7] ................................................ C12N 15/09

(52) U.S. Cl. .................... 435/69.8; 435/69.1; 435/69.7; 435/71.1

(58) Field of Search ............................... 435/69.1, 69.7, 435/69.8, 71.1

(56) References Cited

U.S. PATENT DOCUMENTS 4,923,808 A 5/1990 Matteucci
5,578,464 A 11/1996 Lunn et al.

FOREIGN PATENT DOCUMENTS

EP 0 955370 A2 11/1999
WO WO 99/42121 8/1999

OTHER PUBLICATIONS

Nelson et al. Lehninger Principles of Biochemistry 3rd ed. Worth Publishers 2000.*

Abo, Tatsuhiko et al., <SsrA–mediated tagging and proteolysis of Lacl and its role in the regulation of lac operon,> EMBO Journal, 19:3762–3769, 2000.

Arima, Hiduyuki et al., <Enhanced secretion of hydrophobic peptide fused lysozyme by the introduction of N–glycosylation signal and the disruption of calnexin gene in *Saccharomyces cerevisiae*,>> FEBS Letters vol. 440, No. 1–2, pp. 89–92, 1998.

Atkins, Johns F. et al., <A case for trans translation,> Nature, 379:769–771, 1996.

Gottesman, Susan et al., <The ClpXP and ClpAP proteases degrade proteins with carboxy–terminal peptide tails added by the SsrA–tagging system,> Genes and Dev., 12:1338–1347, 1998.

Guérout–Fleury, Anne–Marie et al., <Antibiotic–resistance cassettes for *Bacillus subtilis*,> Gene, 167:335–336, 1995.

Hale & Marham, The Harper Collins Dictionary of Microbiology, Harper Perennial, Ny, 1991.

Herman, Christophe, et al., <Degradation of carboxy–terminal–tagged cytoplasmic proteins by the *Escherichia coli* protease HflB (FtsH),> Genes and Dev., 12;1348–1355, 1998.

Jentsch, Stefan, <When Proteins Receive Deadly Messages at Birth,> Science, 271 :955–956, 1996.

Karzai, A. Wali et al., <SmpB, a unique RNA–binding protein essential for the peptide–tagging activity of SsrA (tmRNA),> EMBO J., 18 :3793–3799, 1999.

Karzai, A. Wali et al., <The SsrA–SmpB system for protein tagging, directed degradation and ribosome rescue,> Nat. Struct. Biol., 7 :449–455, No. 7, 2000.

Keller, Kenneth C. et al., <Role of a Peptide Tagging System in Degradation of Proteins'Synthesized from Damaged Messenger RNA, > Science, 271:990–993, 1996.

Kūhn, Sabine et al., <The baculovirus expression vector pBSV–8His directs secretion of histidine–tagged proteins, > *Gene* 162 :225–229 Sep. 11, 1995, XP004042020.

Kunsl, F. et al., <The complete genome sequence of the Gram–positive bacterium *Bacillus subtilis*; > Nature, 390:249–256, 1997.

Muto, Akira et al., <Requirement of transfer–messenger RNA for the growth of *Bacillus subtilis* under stresses, > Genes Cells, 5 :627–635, 2000.

Roche, Eric D. et al., <SsrA–mediated peptide tagging caused by rare codons and tRNA scarcity, > EMBO J., 18:4579–4589, 1999.

Sambrook, J. et al., Molecular Cloning, A Laboratory Manual, 2nd Ed., Cold Spring Harbor Laboratory Press, Cold Spring Harbor, New York, Ch. 9 & 11 1989.

Simonen, Marjo et al., <Protein Secretion in *Bacillus Species*, > Microbiological Reviews, American Society for Microbiology, Washington D.C., U.S. vol. 57, No. 1 Mar. 1, 1993, pp. 109–137.

Singleton et al., Dictionary of Microbiology and Molecular Biology, 2$^{nd}$ ed., John Wiley & Sons, New York, 1994.

Tu, Guo–Fen et al., >C–terminal Extension of Truncated Recombinant Proteins in *Escherichia coli* with a 10Sa RNA Decapeptide,≦ J. Biol. Chem., 270:9322–9326, 1995.

Udaka, Shigezo et al., >High–Level Secretion of Heterologous Proteins by *Bacillus*,≦ Methods in Enzymology, Academic Press, Inc., 217 :23–33, 1993.

Ushida, Chisato et al., >tRNA–like structures in 10Sa RNAs of Mycoplasma capricolum and *Bacillus subtilis*,≦ Nucleic Acids Res., 22:3392–3396, 1994.

(List continued on next page.)

*Primary Examiner*—James Ketter
*Assistant Examiner*—Konstantina Katcheves
(74) *Attorney, Agent, or Firm*—Genencor International, Inc.

(57) ABSTRACT

Described herein are methods for the enhanced production of secreted proteins. The secretion of a protein of interest having a substantially non-polar carboxy tail is enhanced by the placement of charged amino acid residues at the carboxy terminus either by adding to the native peptide or by replacing, i.e., substituting, the terminal residues of the native peptide.

18 Claims, 5 Drawing Sheets

OTHER PUBLICATIONS

Vagner; Valerie et al., >A vector for systematic gene inactivation in *Bacillus subtilis*,≦ Microbiology, 144 :3097–3104, 1998.

Van Diji, Jan Maarten et al., >Non–functional expression of Escherichia coli signal peptides I in Bacilis subtilis,≦ J. Gen. Microbiol., 137:2073–2083, 1991.

Van Leon, Rob W. et al., >Production of Human Interleukin–3 Using Industrial Microorganisms,≦ Biotechnology, 9 :47–52, 1991.

Wiegart, Thomas et al., >SsrA–Mediated Tagging in Bacillus subtilis,≦ J. Bacterial., 183 :3885–3889, 2001.

Williams, Kelly P., >The tmRNA Website,≦ Nucleic Acids Re., 28 :168, 2000.

Williams, Kelly P. et al., >Resuming translation on tmRNA : an unique mode of determining a reading frame, ≦ EMBO J., 18 :5423–5433, 1999.

Wu, Xu–Chu, >Engineering a Bacillus subtilis Expression–Secretion System with a Strain Deficient in Six Extracellustar Proteases,≦ J. Bacteriol., 173 :4952–4958, 1991.

PCT International Search Report.

* cited by examiner

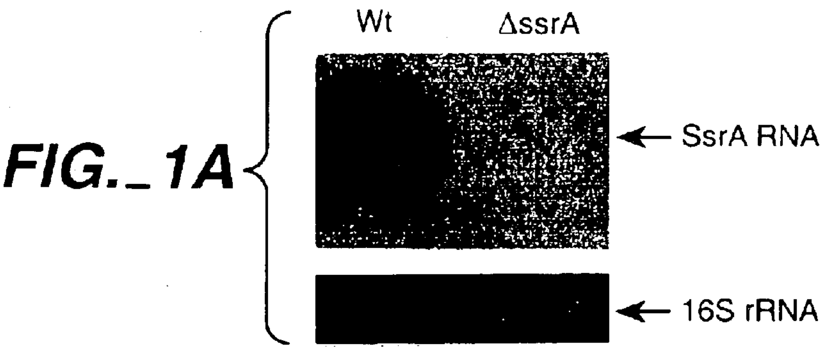
FIG._1A
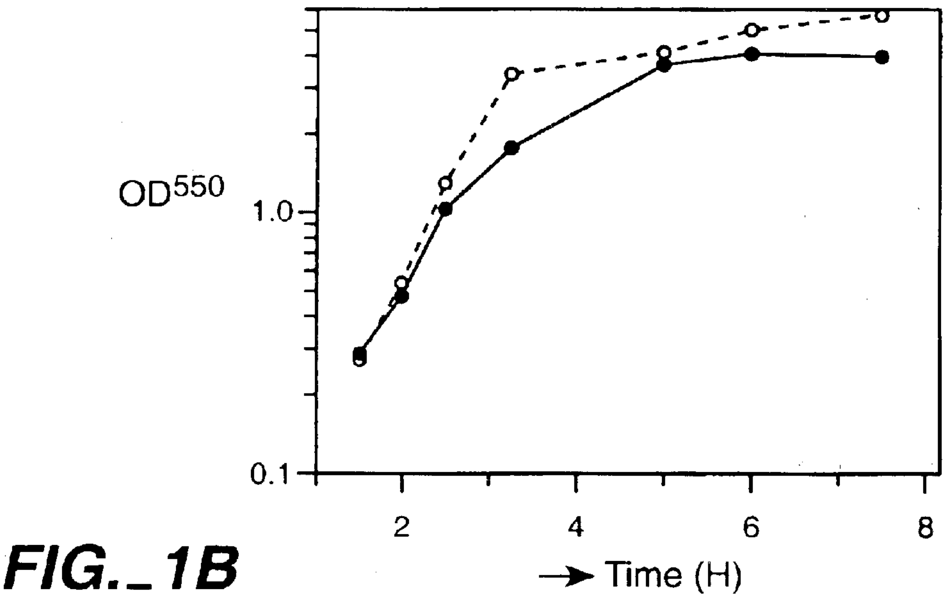
FIG._1B
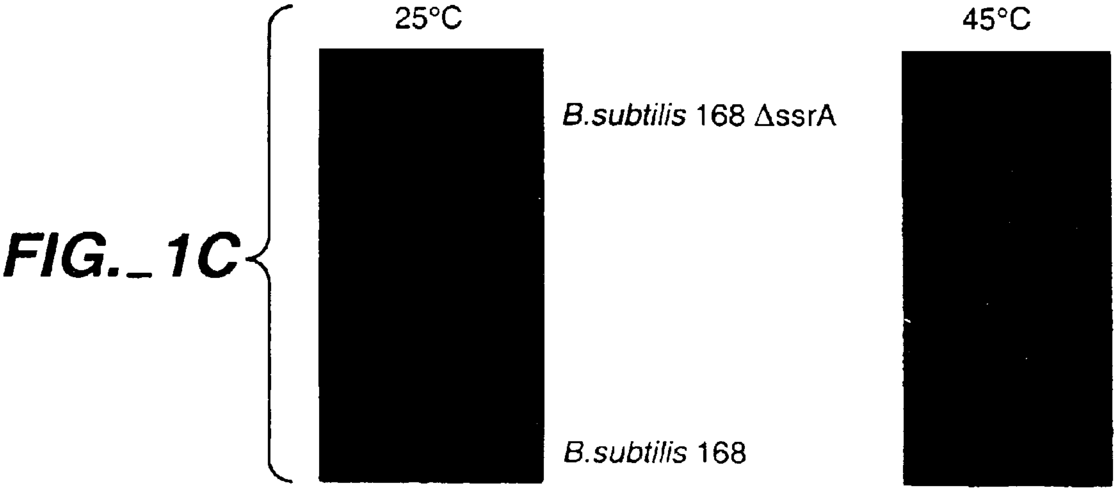
FIG._1C

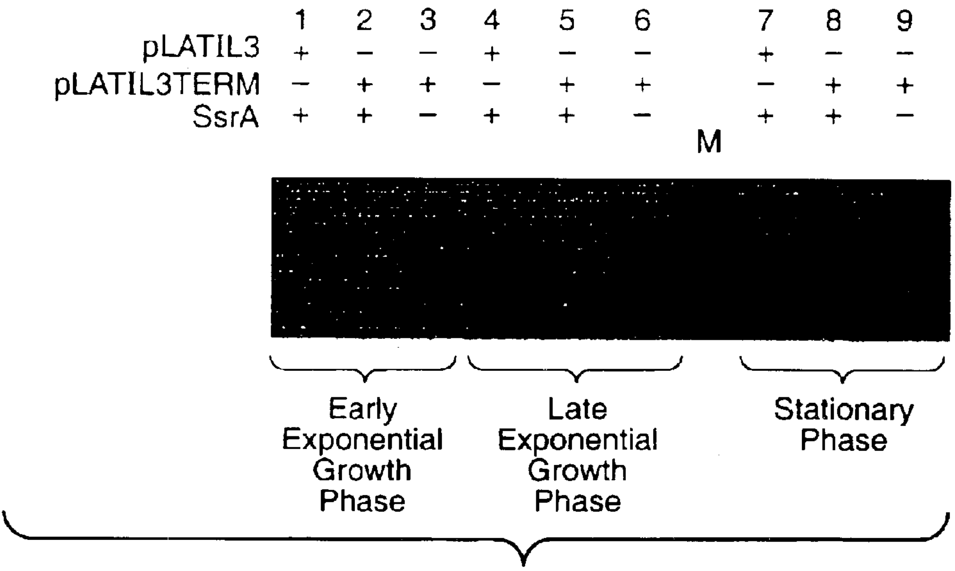
*FIG._2*
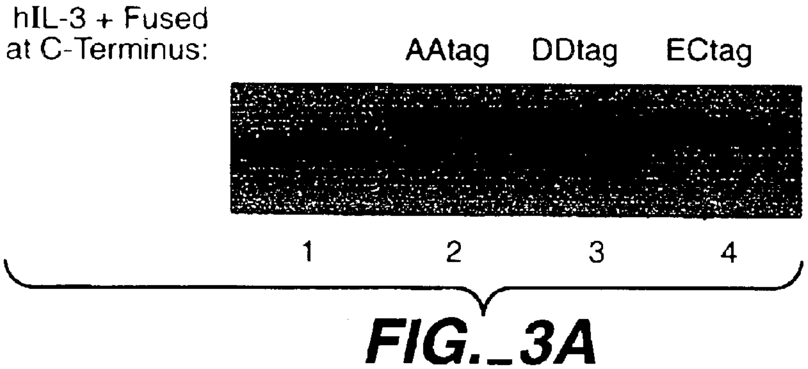
*FIG._3A*
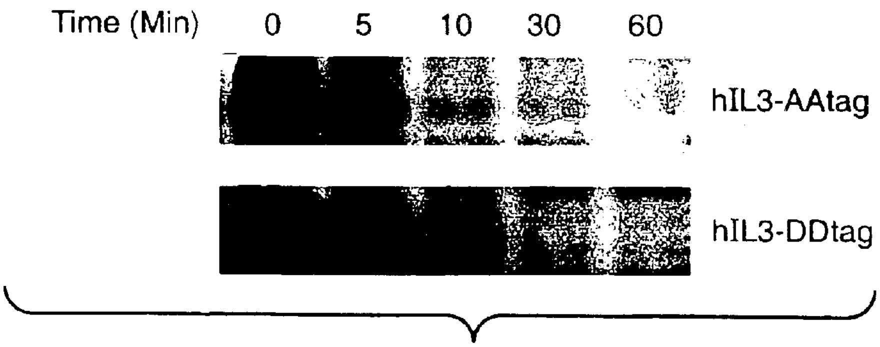
*FIG._3B*

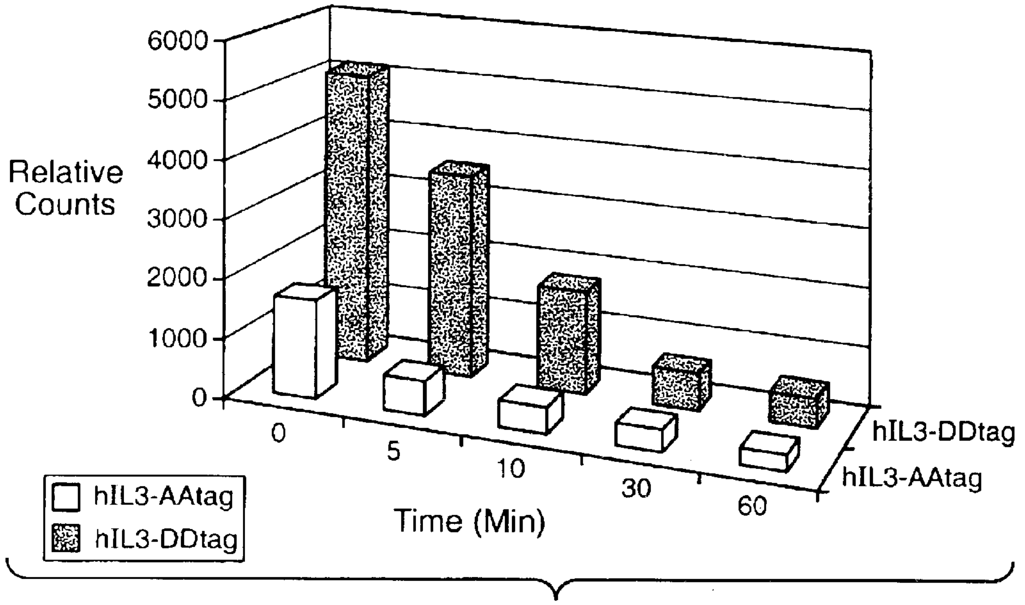
FIG._3C
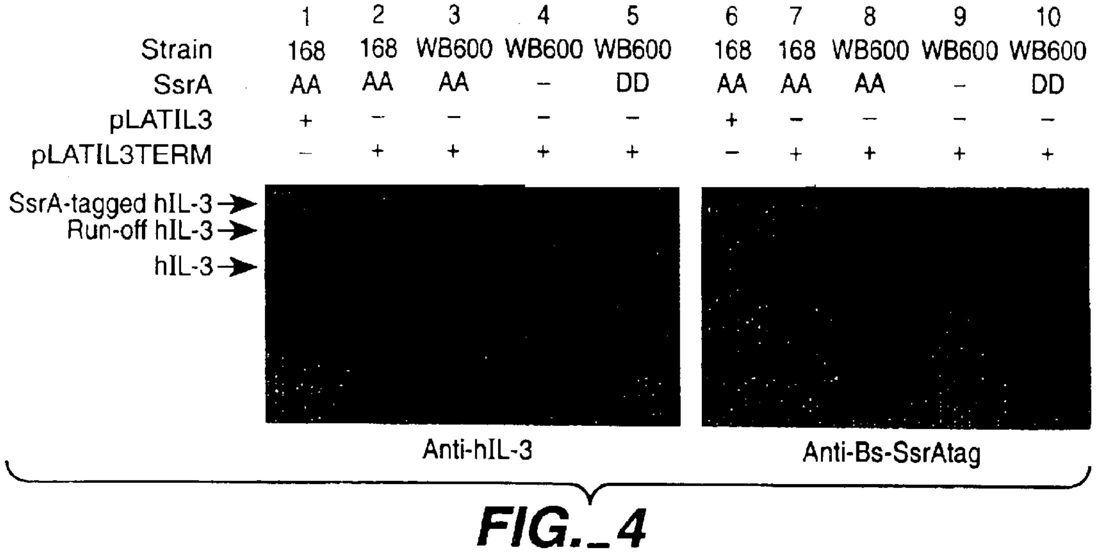
FIG._4

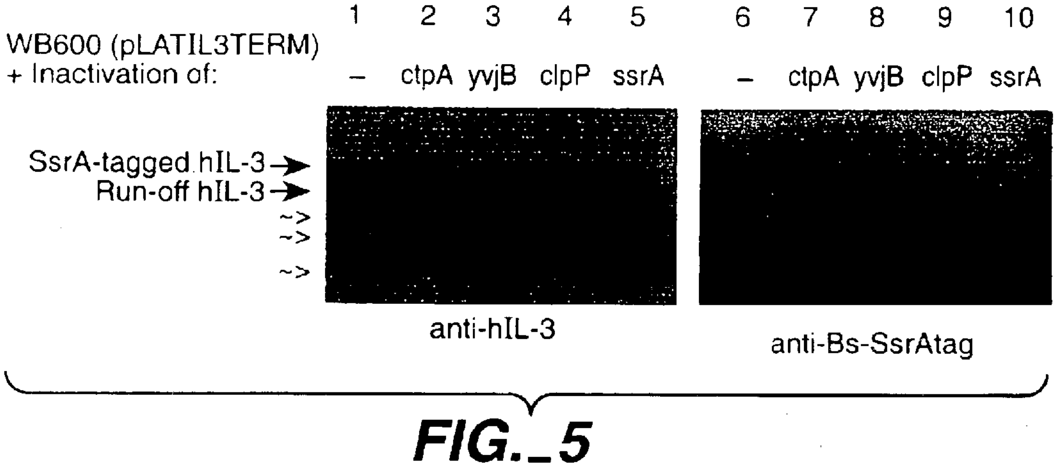
FIG._5
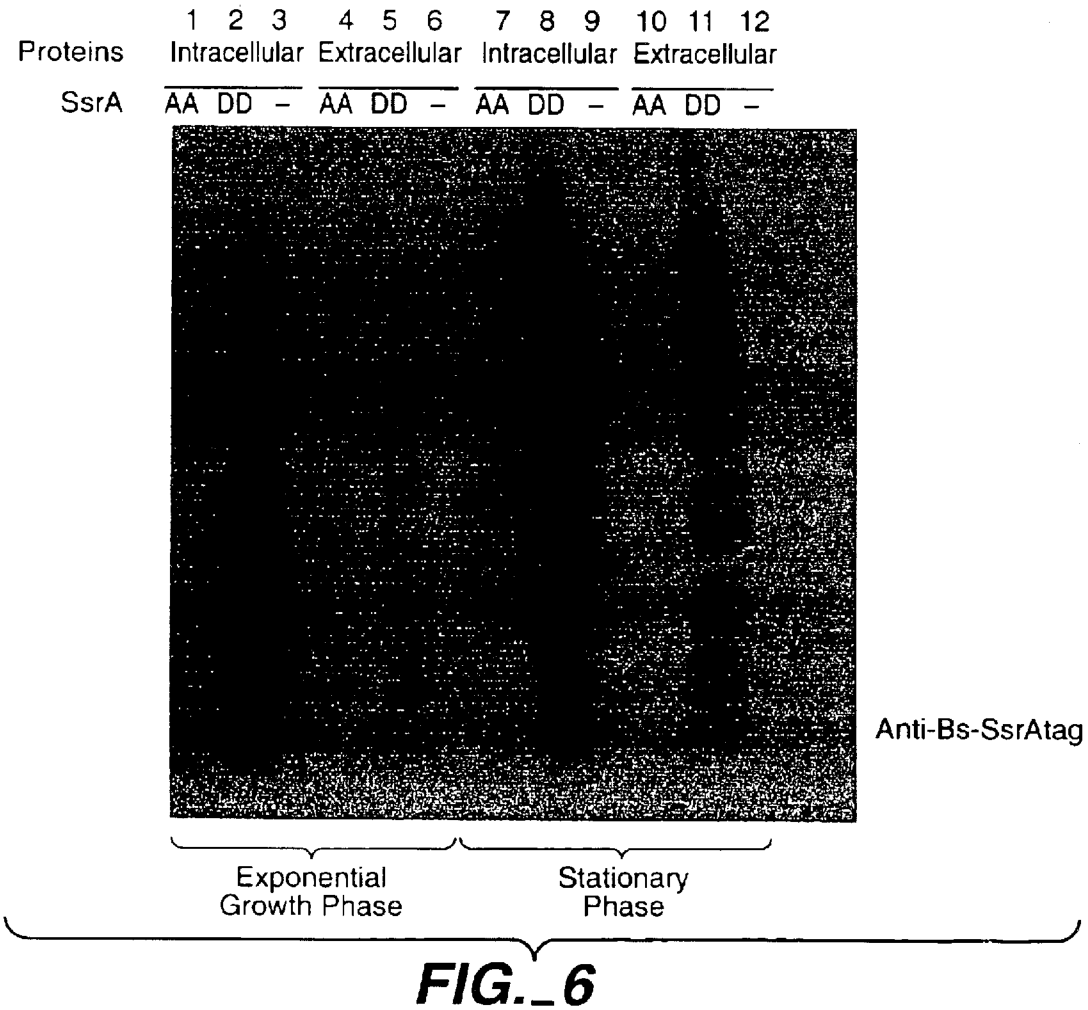
FIG._6

IL-3 amino acid sequence (Native sequence associated with its native signal sequence)

MSRLPVLLLL QLLVRPGLQA PMTQTTPLKT SWVNCSNMID
EIITHLKQPP
LPLLDFNNLN GEDQDILMEN NLRRPNLEAF NRAVKSLQNA
SAIESILKNL
LPCLPLATAA PTRHPIHIKD GDWNEFRRKL TFYLKTLENA
QAQQTTLSLA IF

IL-3 as encoded by plasmid pLATIL3

MKQQKRLYAR LLTLLFALIF LLPHSSASAA PMTQTTPLKT SWVNCSNMID
EIITHLKQPP LPLLDFNNLN GEDQDILMEN NLRRPNLEAF NRAVKSLQNA
SAIESILKNL LPCLPLATAA PTRHPIHIKD GDWNEFRRKL TFYLKTLENA
QAQQTTLS

IL-3 amino acid sequence (Substituted tag charged C-terminus)

MKQQKRLYAR LLTLLFALIF LLPHSSASAA PMTQTTPLKT SWVNCSNMID
EIITHLKQPP LPLLDFNNLN GEDQDILMEN NLRRPNLEAF NRAVKSLQNA
SAIESILKNL LPCLPLATAA PTRHPIHIKD GDWNEFRRKL TFYLKTLENA
QAQQTT*DD*

IL-3 amino acid sequence (Tagged[14])

MKQQKRLYAR LLTLLFALIF LLPHSSASAA PMTQTTPLKT SWVNCSNMID
EIITHLKQPP LPLLDFNNLN GEDQDILMEN NLRRPNLEAF NRAVKSLQNA
SAIESILKNL LPCLPLATAA PTRHPIHIKD GDWNEFRRKL TFYLKTLENA
QAQQTTLS*AG KTNSFNQNVA LDD*

FIG._7

SEQUENCE LISTING

```
<160> NUMBER OF SEQ ID NOS: 30

<210> SEQ ID NO 1
<211> LENGTH: 15
<212> TYPE: PRT
<213> ORGANISM: Artificial Sequence
<220> FEATURE:
<223> OTHER INFORMATION: synthetic peptide tag

<400> SEQUENCE: 1

Ala Gly Lys Thr Asn Ser Phe Asn Gln Asn Val Ala Leu Ala Ala
 1               5                  10                  15


<210> SEQ ID NO 2
<211> LENGTH: 15
<212> TYPE: PRT
<213> ORGANISM: Artificial Sequence
<220> FEATURE:
<223> OTHER INFORMATION: synthetic peptide tag

<400> SEQUENCE: 2

Ala Gly Lys Thr Asn Ser Phe Asn Gln Asn Val Ala Leu Asp Asp
 1               5                  10                  15


<210> SEQ ID NO 3
<211> LENGTH: 11
<212> TYPE: PRT
```

-continued

<213> ORGANISM: Artificial Sequence
<220> FEATURE:
<223> OTHER INFORMATION: synthetic peptide tag

<400> SEQUENCE: 3

Ala Ala Asn Asp Glu Asn Tyr Ala Leu Ala Ala
1 5 10

<210> SEQ ID NO 4
<211> LENGTH: 15
<212> TYPE: PRT
<213> ORGANISM: Artificial Sequence
<220> FEATURE:
<223> OTHER INFORMATION: synthetic peptide tag

<400> SEQUENCE: 4

Ala Gly Lys Thr Asn Ser Phe Asn Gln Asn Val Ala Leu Lys Lys
1 5 10 15

<210> SEQ ID NO 5
<211> LENGTH: 14
<212> TYPE: PRT
<213> ORGANISM: Artificial Sequence
<220> FEATURE:
<223> OTHER INFORMATION: synthetic peptide tag

<400> SEQUENCE: 5

Gly Lys Thr Asn Ser Phe Asn Gln Asn Val Ala Leu Ala Ala
1 5 10

<210> SEQ ID NO 6
<211> LENGTH: 14
<212> TYPE: PRT
<213> ORGANISM: Artificial Sequence
<220> FEATURE:
<223> OTHER INFORMATION: synthetic peptide tag

<400> SEQUENCE: 6

Gly Lys Thr Asn Ser Phe Asn Gln Asn Val Ala Leu Asp Asp
1 5 10

<210> SEQ ID NO 7
<211> LENGTH: 32
<212> TYPE: DNA
<213> ORGANISM: Artificial Sequence
<220> FEATURE:
<223> OTHER INFORMATION: primer

<400> SEQUENCE: 7
gtcgacctcg agaccccaag cttggcgtaa tc 32

<210> SEQ ID NO 8
<211> LENGTH: 60
<212> TYPE: DNA
<213> ORGANISM: Artificial Sequence
<220> FEATURE:
<223> OTHER INFORMATION: primer

<400> SEQUENCE: 8
gtcgacctcg agcggcagaa tcttttttg attctgccgc aaagtcgtct gttgagcctg 60

<210> SEQ ID NO 9
<211> LENGTH: 71
<212> TYPE: DNA
<213> ORGANISM: Artificial Sequence
<220> FEATURE:
<223> OTHER INFORMATION: primer -continued

<400> SEQUENCE: 9
ctgcagctcg aggatatcgt cgaccggcag aatcaaaaaa agattctgcc gaccccaagc 60
ttggcgtaat c 71

<210> SEQ ID NO 10
<211> LENGTH: 81
<212> TYPE: DNA
<213> ORGANISM: Artificial Sequence
<220> FEATURE:
<223> OTHER INFORMATION: primer

<400> SEQUENCE: 10
cttctactcg agtcaggcag ctaatgctac gttttggtta aaactgttag ttttgcctgc 60
gctcaaagtc gtctgttgag c 81

<210> SEQ ID NO 11
<211> LENGTH: 81
<212> TYPE: DNA
<213> ORGANISM: Artificial Sequence
<220> FEATURE:
<223> OTHER INFORMATION: primer

<400> SEQUENCE: 11
cttctactcg agtcagtcgt ctaatgctac gttttggtta aaactgttag ttttgcctgc 60
gctcaaagtc gtctgttgag c 81

<210> SEQ ID NO 12
<211> LENGTH: 69
<212> TYPE: DNA
<213> ORGANISM: Artificial Sequence
<220> FEATURE:
<223> OTHER INFORMATION: primer

<400> SEQUENCE: 12
cttctactcg agtcaagctg ctaaagcgta gttttcgtcg tttgctgcgc tcaaagtcgt 60
ctgttgagc 69

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
cagctccgtc tgaggaaaaa g 21

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
cgaagtgggc gatttcttcc g 21

<210> SEQ ID NO 15
<211> LENGTH: 40
<212> TYPE: DNA
<213> ORGANISM: Artificial Sequence
<220> FEATURE:

-continued

<223> OTHER INFORMATION: primer

<400> SEQUENCE: 15
ttctaaaagc ttagtgcttg attcgaaaat caggcctgtg 40

<210> SEQ ID NO 16
<211> LENGTH: 45
<212> TYPE: DNA
<213> ORGANISM: Artificial Sequence
<220> FEATURE:
<223> OTHER INFORMATION: primer

<400> SEQUENCE: 16
gagctcgctg cgcttattag tcgtctaatg ctacgttttg gttaa 45

<210> SEQ ID NO 17
<211> LENGTH: 45
<212> TYPE: DNA
<213> ORGANISM: Artificial Sequence
<220> FEATURE:
<223> OTHER INFORMATION: primer

<400> SEQUENCE: 17
ttaaccaaaa cgtagcatta gacgactaat aagcgcagcg agctc 45

<210> SEQ ID NO 18
<211> LENGTH: 40
<212> TYPE: DNA
<213> ORGANISM: Artificial Sequence
<220> FEATURE:
<223> OTHER INFORMATION: primer

<400> SEQUENCE: 18
cctccgtgca tgcttcctct tatttattga cagaaatctg 40

<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19
agagttttaa atctctcggg agaaacacat ggatgacatt 40

<210> SEQ ID NO 20
<211> LENGTH: 40
<212> TYPE: DNA
<213> ORGANISM: Artificial Sequence
<220> FEATURE:
<223> OTHER INFORMATION: primer

<400> SEQUENCE: 20
tgtatatgta aatttcagat catcataaat atctgctatt 40

<210> SEQ ID NO 21
<211> LENGTH: 31
<212> TYPE: DNA
<213> ORGANISM: Artificial Sequence
<220> FEATURE:
<223> OTHER INFORMATION: primer

<400> SEQUENCE: 21
cttaccgaat tcgtgaagga ggagcattat g 31

-continued

```
<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22

gcctttggat ccggctgcaa gcaggaacgc                                        30


<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23

acgttacgga ttcgacaggg atgg                                              24


<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24

gagtcgaacc cacgtccaga aa                                                22


<210> SEQ ID NO 25
<211> LENGTH: 152
<212> TYPE: PRT
<213> ORGANISM: Bacillus subtilis

<400> SEQUENCE: 25

Met Ser Arg Leu Pro Val Leu Leu Leu Leu Gln Leu Leu Val Arg Pro
 1               5                  10                  15

Gly Leu Gln Ala Pro Met Thr Gln Thr Thr Pro Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150


<210> SEQ ID NO 26
<211> LENGTH: 158
<212> TYPE: PRT
<213> ORGANISM: Artificial Sequence
<220> FEATURE:
```

-continued

<223> OTHER INFORMATION: IL-3 encoded by plasmid pLATIL-3

<400> SEQUENCE: 26

```
Met Lys Gln Gln Lys Arg Leu Tyr Ala Arg Leu Leu Thr Leu Leu Phe
 1               5                  10                  15

Ala Leu Ile Phe Leu Leu Pro His Ser Ser Ala Ser Ala Ala Pro Met
            20                  25                  30

Thr Gln Thr Thr Pro Leu Lys Thr Ser Trp Val Asn Cys Ser Asn Met
        35                  40                  45

Ile Asp Glu Ile Ile Thr His Leu Lys Gln Pro Pro Leu Pro Leu Leu
    50                  55                  60

Asp Phe Asn Asn Leu Asn Gly Glu Asp Gln Asp Ile Leu Met Glu Asn
65                  70                  75                  80

Asn Leu Arg Arg Pro Asn Leu Glu Ala Phe Asn Arg Ala Val Lys Ser
               85                  90                  95

Leu Gln Asn Ala Ser Ala Ile Glu Ser Ile Leu Lys Asn Leu Leu Pro
            100                 105                 110

Cys Leu Pro Leu Ala Thr Ala Ala Pro Thr Arg His Pro Ile His Ile
        115                 120                 125

Lys Asp Gly Asp Trp Asn Glu Phe Arg Arg Lys Leu Thr Phe Tyr Leu
    130                 135                 140

Lys Thr Leu Glu Asn Ala Gln Ala Gln Gln Thr Thr Leu Ser
145                 150                 155
```

<210> SEQ ID NO 27
<211> LENGTH: 158
<212> TYPE: PRT
<213> ORGANISM: Artificial Sequence
<220> FEATURE:
<223> OTHER INFORMATION: IL-3 substituted tag chanrged C-terminus

<400> SEQUENCE: 27

```
Met Lys Gln Gln Lys Arg Leu Tyr Ala Arg Leu Leu Thr Leu Leu Phe
 1               5                  10                  15

Ala Leu Ile Phe Leu Leu Pro His Ser Ser Ala Ser Ala Ala Pro Met
            20                  25                  30

Thr Gln Thr Thr Pro Leu Lys Thr Ser Trp Val Asn Cys Ser Asn Met
        35                  40                  45

Ile Asp Glu Ile Ile Thr His Leu Lys Gln Pro Pro Leu Pro Leu Leu
    50                  55                  60

Asp Phe Asn Asn Leu Asn Gly Glu Asp Gln Asp Ile Leu Met Glu Asn
65                  70                  75                  80

Asn Leu Arg Arg Pro Asn Leu Glu Ala Phe Asn Arg Ala Val Lys Ser
               85                  90                  95

Leu Gln Asn Ala Ser Ala Ile Glu Ser Ile Leu Lys Asn Leu Leu Pro
            100                 105                 110

Cys Leu Pro Leu Ala Thr Ala Ala Pro Thr Arg His Pro Ile His Ile
        115                 120                 125

Lys Asp Gly Asp Trp Asn Glu Phe Arg Arg Lys Leu Thr Phe Tyr Leu
    130                 135                 140

Lys Thr Leu Glu Asn Ala Gln Ala Gln Gln Thr Thr Asp Asp
145                 150                 155
```

<210> SEQ ID NO 28
<211> LENGTH: 173
<212> TYPE: PRT
<213> ORGANISM: Artificial Sequence -continued

```
<220> FEATURE:
<223> OTHER INFORMATION: tagged IL-3 amino acid

<400> SEQUENCE: 28

Met Lys Gln Gln Lys Arg Leu Tyr Ala Arg Leu Leu Thr Leu Leu Phe
 1              5                  10                  15

Ala Leu Ile Phe Leu Leu Pro His Ser Ser Ala Ser Ala Ala Pro Met
            20                  25                  30

Thr Gln Thr Thr Pro Leu Lys Thr Ser Trp Val Asn Cys Ser Asn Met
        35                  40                  45

Ile Asp Glu Ile Ile Thr His Leu Lys Gln Pro Pro Leu Pro Leu Leu
    50                  55                  60

Asp Phe Asn Asn Leu Asn Gly Glu Asp Gln Asp Ile Leu Met Glu Asn
65                  70                  75                  80

Asn Leu Arg Arg Pro Asn Leu Glu Ala Phe Asn Arg Ala Val Lys Ser
                85                  90                  95

Leu Gln Asn Ala Ser Ala Ile Glu Ser Ile Leu Lys Asn Leu Leu Pro
            100                 105                 110

Cys Leu Pro Leu Ala Thr Ala Ala Pro Thr Arg His Pro Ile His Ile
        115                 120                 125

Lys Asp Gly Asp Trp Asn Glu Phe Arg Arg Lys Leu Thr Phe Tyr Leu
    130                 135                 140

Lys Thr Leu Glu Asn Ala Gln Ala Gln Gln Thr Thr Leu Ser Ala Gly
145                 150                 155                 160

Lys Thr Asn Ser Phe Asn Gln Asn Val Ala Leu Asp Asp
                165                 170


<210> SEQ ID NO 29
<211> LENGTH: 15
<212> TYPE: PRT
<213> ORGANISM: Artificial Sequence
<220> FEATURE:
<223> OTHER INFORMATION: synthetic peptide tag

<400> SEQUENCE: 29

Ala Gly Lys Thr Asn Ser Phe Asn Gln Asn Val Ala Leu Glu Glu
 1              5                  10                  15


<210> SEQ ID NO 30
<211> LENGTH: 15
<212> TYPE: PRT
<213> ORGANISM: synthetic peptide tag

<400> SEQUENCE: 30

Ala Gly Lys Thr Asn Ser Phe Asn Gln Asn Val Ala Leu Arg Arg
 1              5                  10                  15
```

ENHANCED SECRETION OF A POLYPEPTIDE BY A MICROORGANISM

CROSS-REFERENCE TO RELATED APPLICATIONS

Pursuant to 35 U.S.C. §119(e), the present application claims benefit of and priority to U.S. Ser. No. 60/239,531, entitled "Enhanced Secretion of a Polypeptide by a Microorganism", filed Oct. 10, 2000, by Marc Kolkman.

FIELD OF THE INVENTION

This invention relates to the production and secretion of a selected polypetide. More particularly, the present invention provides for the enhanced secretion of a selected polypeptide by a microorganism, such as a *Bacillus* species.

BACKGROUND OF THE INVENTION

Eubacteria export numerous proteins across the plasma membrane into either the periplasmic space (Gram-negative species), or the growth medium (Gram-positive species). The Gram-positive eubacterium *Bacillus subtilis* and, in particular, its close relatives *Bacillus amyloliquefaciens* and *Bacillus licheniformis* are well known for their high capacity to secrete proteins (at gram per liter concentrations) into the medium. This property, which allows the efficient separation of (secreted) proteins from the bulk cytoplasmic protein complement, has led to the commercial exploitation of the latter bacilli as important "cell factories." Despite their high capacity to secrete proteins of Gram-positive origin, the secretion of recombinant proteins from Gram-negative eubacterial or eukaryotic origin by *Bacillus* species is often inefficient.

General strategies for the secretion of heterologous proteins by bacilli are based on the in-frame fusion of the respective protein with an amino-terminal signal peptide that directs this protein into a secretion pathway, for example the Sec-dependent secretory pathway. Upon translocation across the membrane, the signal peptide is removed by a signal peptidase, which is a prerequisite for the release of the translocated protein from the membrane, and its secretion into the medium.

Proteolysis in bacteria serves to rid the cell of abnormal, and misfolded proteins. A unique mechanism for the destruction of abnormal proteins resulting from abortive termination of translation is provided by the SsrA-mediated tagging and degradation system (for a recent review, see Karzai et al. (2000). The SsrA-SmpB system for protein tagging, directed degradation and ribosome rescue. Nat. Struct. Biol. 7:449–455.). SsrA, also called 10Sa RNA or tmRNA is a highly conserved RNA molecule in eubacteria. It is a unique molecule that can act as both a tRNA and an mRNA in a process referred to as trans-translation (Atkins et al. 1996. A case for trans translation. Nature 379:769–771, Jentsch 1996. When proteins receive deadly messages at birth. Science 271:955–956, Keiler et al. 1996. Role of a peptide tagging system in degradation of proteins synthesized from damaged messenger RNA. Science 271:990–993). This mechanism provides the cell a way to release ribosomes that are stalled on untranslatable mRNAs, e.g. mRNAs lacking in-frame stop codons. In the model for SsrA action, SsrA charged with alanine enters the A site of a stalled ribosome, mimicking a tRNA. The alanine is added to the uncompleted polypeptide chain; and then, serving as an mRNA, SsrA provides a short reading frame followed by a stop codon as a template to add a short peptide to the nascent polypeptide before translation terminates and a tagged protein is released. The peptide tag (encoded by SsrA) functions as a proteolytic degradation signal, and in *Escherichia coli* four proteases have been identified that degrade proteins tagged by SsrA. ClpXP, ClpAP, and FtsH (HflB) degrade SsrA tagged proteins in the cytoplasm (Gottesman et al. 1998. The ClpXP and ClpAP proteases degrade proteins with carboxy-terminal peptide tails added by the SsrA-tagging system. Genes Dev. 12:1338–1347, Herman et al. 1998. Degradation of carboxy-terminal-tagged cytoplasmic proteins by the *Escherichia coli* protease HflB (FtsH). Genes Dev. 12:1348–1355), while SsrA tagged proteins with signal peptides that are exported to the periplasm of *E. coli* are degraded by Tsp (Prc) protease (Keiler et al. 1996).

Protein production and secretion from Bacillus species is a major production tool with a market of over $1 billion per year. However, proteolysis of proteins by endogenous proteases diminishes the production capability of these microorganisms. Thus, it would be beneficial to have an mechanism for the enhanced production and secretion proteins. The present invention provides such an advantage by changing the nonpolar C-terminus of a protein by adding charged, polar residues (or by replacing amino acids), so that the proteins are protected against the bacillus proteases that degrade SsrA-tagged proteins.

SUMMARY OF THE INVENTION

Provided herein are methods for the enhanced production of peptides in a host cell.

In one aspect of the invention, the present invention provides methods for increasing secretion of proteins from host microorganisms. In one embodiment of the present invention, the protein is homologous or naturally occurring in the host microorganism. In another embodiment of the present invention, the protein is heterologous to the host microorganism. Accordingly, the present invention provides a method for increasing secretion of a protein in a host cell using an expression vector comprising nucleic acid sequence encoding a protein of interest wherein said nucleic acid sequence is under the control of expression signals capable of expressing said protein of interest in a host microorganism; introducing the expression vector into a host microorganism capable of expressing said protein and culturing said microorganism under conditions suitable for expression of said secretion factor and secretion of said protein.

In one embodiment, the host cell is transformed with a first DNA sequence encoding a signal peptide operably linked to a second DNA sequence encoding a protein. Said protein may be, but not limited to, hormones, enzymes, growth factors, cytokines, antibodies and the like. In another embodiment, the enzyme includes, but is not limited to hydrolases, such as protease, esterase, lipase, phenol oxidase, permease, amylase, pullulanase, cellulase, glucose isomerase, laccase and protein disulfide isomerase. The second DNA sequence may encode a protein that has been modified such that its carboxy-terminus possesses at least one, preferably two, charged amino acids. Such modification may be by substitution of the native carboxy-terminal residues or addition of a tag sequence to the native protein's carboxy-terminus.

Further provided herein is a method of enhancing resistance to proteolysis of a protein. In a preferred embodiment the protein is a secreted protein. It is contemplated that the protein will comprise a tag wherein the tag comprises at least one charged amino acid residue. The charged amino acid residue may be either a positively charged residue or it may be a negatively charged residue.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE FIGURES

FIG. 1. A. Northern blot of total RNA of *B. subtilis* 168 and *B. subtilis* 168 ΔssrA, hybridized with an ssrA specific probe. At the bottom: the level of 16S RNA in both RNA samples. B. Growth curves of *B. subtilis* 168 (---○---) and *B. subtilis* 168 ΔssrA (—●—) at 37° C. in TSB medium. C. Growth of *B. subtilis* 168 and *B. subtilis* 168 ΔssrA on Hi-agar plates at 25° C. or 45° C.

FIG. 2. hIL-3 expressed from an mRNA without a stop codon (pLATIL3TERM), accumulates in the medium of *B. subtilis* lacking SsrA (lanes 3, 6, 9), but not in cells containing functional SsrA (lanes 2, 5, 8). At three different growth stages, samples were collected from cultures of *B. subtilis* 168 (pLATIL3) [lanes 1, 4, 7], *B. subtilis* 168 (pLATIL3TERM) [lanes 2, 5, 8], and *B. subtilis* 168 ΔssrA (pLATIL3TERM) [lane 3, 6, 9]. After centrifugation, the proteins in the culture supernatants were concentrated by TCA precipitation and analyzed by SDS-PAGE and Western blotting with anti-hIL-3 antibodies. The amount of total extracellular protein of *B. subtilis* 168 (pLATIL3) that was applied to the gel [lanes 1, 4, 7] was 10 times less then that of *B. subtilis* 168 (pLATIL3TERM) [lanes 2, 5, 8] or *B. subtilis* 168 ΔssrA (pLATIL3TERM) [lanes 3, 6, 9]. M indicates a lane with a prestained protein ladder; the molecular weight of the upper band corresponds to 20 kDa, that of the lower band to 15 kDa.

FIG. 3. Stability of hIL-3 variants with different C-terminal tags.

(A). Western blot analysis of hIL-3 protein variants produced by *B. subtilis* 168 transformed with plasmid pLATIL3 (lane 1), pLATIL3BStag (expression of hIL-3 with a C-terminal *B. subtilis* SsrA tag (AA-tag): hIL-3-AGKTNSFNQNVALAA (SEQ ID NO:1); lane 2), pLATIL3DDtag (expression of hIL-3 with a DD-tag: hIL-3-AGKTNSFNQNVALDD (SEQ ID NO:2); lane 3), and pLATIL3ECtag (expression of hIL-3 with a C-terminal *E. coli* SsrA tag (EC-tag): hIL-3-AANDENYALAA (SEQ ID NO:3); lane 4). Culture supernatants of cells entering the stationary phase were collected and analyzed by SDS-PAGE and Western blotting with anti-hIL-3 antibody.

(B). Pulse-chase assays: Cells of *B. subtilis* 168 (pLATIL3BStag) and 168 (pLATIL3DDtag) were labeled with [$^{35}$S]-methionine for 1' prior to chase with excess non-radioactive methionine. Samples were withdrawn at the times indicated, centrifuged and the culture supernatants were analyzed by SDS-PAGE and fluorography.

(C). The amounts of hIL-3-AAtag and hIL3-DDtag in (B) were quantified by determination of the radioactivity in the dried gel using a PhosphorImager (Molecular Dynamics) and plotted.

FIG. 4. The 'major extracellular proteases' of *B. subtilis* play a role in the degradation of extracellular, SsrA-tagged h-IL3. Western blot analysis of hIL-3 protein secreted by *B. subtilis* 168 harboring plasmid pLATIL3 (lane 1, 6) or pLATIL3TERM (lane 2, 7), and *B. subtilis* WB600 (a multiple protease negative strain) containing plasmid pLATIL3TERM and expressing either wild-type SsrA (lane 3, 8), no SsrA (lane 4, 9) or SsrA$^{DD}$ (lane 5, 10). Culture supernatants of cells entering the stationary phase were collected, concentrated by TCA precipitation, analyzed by SDS-PAGE and immunoblotting with anti-hIL-3 antibody (lanes 1–5) or anti-Bs-SsrAtag antibody (lanes 6–10). SsrA-tagged hIL-3 (lanes 3, 5, 8, 10), run-off hIL-3 translation product (lane 4, and possibly also in lane 3 and 5, see text), and wild-type hIL-3 (lane 1) are indicated by the arrows (→). Protein bands with lower molecular weight that also react with anti-hIL-3 antibody are supposedly degradation products of hIL-3, SsrA-tagged hIL-3 or run-off hIL-3 translation product.

FIG. 5. *B. subtilis* CtpA has an additional role in the degradation of SsrA-tagged hIL-3. Western blot analysis of hIL-3 protein secreted by *B. subtilis* WB600 harboring plasmid (pLATIL3TERM) and carrying either no additional mutation (lane 1, 6), or lacking CtpA (lane 2, 7), YvjB (lane 3, 8), ClpP (lane 4, 9), or SsrA (lane 5, 10). Culture supernatants of cells entering the stationary phase were collected, concentrated by TCA precipitation, analyzed by SDS-PAGE and Western blotting with anti-hIL-3 antibody (lane 1–5) or anti-Bs-SsrAtag antibody (lane 6–10). The straight arrows (→) mark SsrA-tagged hIL-3 (lanes 1–4 and lanes 6–9), and run-off translation product (lane 5 and possibly (see text) also in lanes 1–4). Degradation products of (SsrA-tagged) hIL-3 are indicated by ~>.

FIG. 6. Tagging of native *B. subtilis* proteins. Total intracellular or extracellular proteins produced by cells in the exponential growth phase or stationary phase of *B. subtilis* 168 expressing wild-type SsrA (AA), 168 IssrA$^{DD}$ expressing SsrA$^{DD}$ (DD), or 168 ΔssrA containing no SsrA RNA (–) were analyzed by Western blotting using anti-Bs-SsrAtag antibody.

FIG. 7. A native protein and examples of the types of tags encompassed by the instant invention. (A) Depicts the sequence of human interleukin-3 (SEQ ID NO:25); the (native) signal peptide is in bold. (B) Depicts the IL-3 sequence encoded by plasmid pLATIL3 (SEQ ID NO:26). The sequence of AmyL[ss]-interleukin-3 is for hIL-3 secretion in *Bacillus*: the AmyL signal peptide is in bold, and this expressed IL-3 lacks the last four amino acids (LAIF) of native hIL-3. The tag is in italics. (C) Depicts IL-3 with a tag that is a substitution of the native protein's terminal two amino acids (SEQ ID NO:27). The tag is in italics. (D) Depicts a tag that is an addition to the native protein's carboxy terminus (SEQ ID NO:28). Here the sequence of hIL3 as encoded by pLATIL3 with the SsrA-DD tag at the C-terminus [hIL3-DD] (signal peptide in bold, C-terminal tag in italics) is shown.

DETAILED DESCRIPTION OF THE INVENTION

The invention will now be described in detail by way of reference only using the following definitions and examples. All patents and publications, including all sequences disclosed within such patents and publications, referred to herein are expressly incorporated by reference.

The present invention provides for a process to enhance the production of a desired secreted polypeptide by a suitable host cell. In particular, the present invention may be applicable to increase protein production by *B. subtilis*. Changing the last two C-terminal amino acids residues into at least one, preferably two, charged amino acid residues or adding at least one, preferably two, charged amino acid residues to the COOH-terminus of a protein may be used to increase the yield of any protein secreted by *B. subtilis*. A longer tag sequence may be utilized in the present invention. Especially the secretion of proteins that have a pl value>7 may be improved by this concept. In general, the minor alteration (adding or replacing two amino acid residues) itself should not lead to a dramatic change in e.g. the specific activity of an enzyme or the thermostablity.

Definitions

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. The headings provided herein are not limitations of the various aspects or embodiments of the invention which can be had by reference to the specification as a whole. Accordingly, the terms defined immediately below are more fully defined by reference to the specification as a whole.

Host Cell

"Host cell" means a cell that has the capacity to act as a host and expression vehicle for an expression cassette according to the invention. In one embodiment, the host cell is a microorganism. In a preferred embodiment according to the present invention, "host cell" means the cells of *Bacillus*. As used herein, the genus Bacillus includes all members known to those of skill in the art, including but not limited to *B. subtilis, B. licheniformis, B. lentus, B. brevis, B. stearothermophilus, B. alkalophilus, B. amyloliquefaciens, B. coagulans, B. ciculans, B. lautus* and *B. thuringiensis*. Other cells useful in the present invention include Acinetobacter, Thermus, Deinococcus Radiodurans.

Polypeptide or Protein

The term "polypeptide" as used herein refers to a compound made up of amino acid residues linked by peptide bonds. The term "protein" as used herein may be synonymous with the term "polypeptide" or may refer, in addition, to a complex of two or more polypeptides.

Additionally, a "protein of interest" or "polypeptide of interest" refers to the protein to be expressed and secreted by the host cell. The protein of interest may be any protein that up until now has been considered for expression in prokaryotes. The protein of interest may be either homologous or heterologous to the host.

The term "chimeric polypeptide" and "fusion polypeptide" are used interchangeably herein and refer to a protein that comprises at least two separate and distinct regions that may or may not originate from the same protein. For example, a signal peptide linked to the protein of interest wherein the signal peptide is not normally associated with the protein of interest would be termed a chimeric polypeptide or chimeric protein.

Signal Sequence

A "signal peptide" as used herein refers to an amino-terminal extension on a protein to be secreted. "Signal sequence" is used interchangeably herein. Nearly all secreted proteins use an amino-terminal protein extension which plays a crucial role in the targeting to and translocation of precursor proteins across the membrane and which is proteolytically removed by a signal peptidase during or immediately following membrane transfer.

In preferred embodiments the signal sequence is selected from sec-dependent signal peptides or tat-dependent signal peptides derived from *Bacillus.*

Enhanced

The present invention is directed to the enhanced production and secretion of a protein of interest. When discussing expression enhanced has the following meanings. In the case a homologous protein enhanced should be read as expression above normal levels in said host. In the case of a heterologous protein basically any expression is, of course, enhanced.

When discussing resistance to proteolysis, enhanced means that the protein of interest has an increased half-life when compared to an altered form of the protein of interest, e.g., untagged.

Non-polar

As used herein, the term "non-polar" refers to the amino acid content of the carboxy tail of a protein. For example, when the last five amino acids at the C-terminus are selected from nonpolar amino acid residues (A, V, L, I, P, F, W, M) the tail is considered nonpolar. If one or two of these last five residues are uncharged polar (G, S, T, C, Y, N, Q), the tail would still be considered substantially nonpolar.

In contrast, if one or two of the last two amino acids at the C-terminus is/are charged polar: D or E (negatively charged) or K, R or H (positively charged), the tail would be considered polar, charged and, according to the present invention, this makes the protein resistant against proteolytic degradation by a subclass of proteases that recognize non-polar C-terminal tails of secreted proteins.

Tag Sequence

As used herein, a "tag sequence" or "tag" refers to a short peptide sequence on the carboxy terminus of an expressed protein that effects the proteolysis of the expressed protein. For example, the bacterial tag encoded by ssrA is cotranslationally added to truncated polypeptides, thereby targeting these molecules for proteolytic degradation. It is to be understood that in the present invention the addition of a tag serves to signal a decrease in proteolytic degradation, i.e., enhanced resistance to proteases, of proteins with substantially non-polar carboxy termini.

Preferably the tag is at least one charged amino acid residue. Preferably, the tag comprises two charged amino acid residues. The charged amino acid residue(s) may be positively charged. Alternatively, the charged amino acid residue(s) may be negatively charged.

The tag should be as short as possible, since the tag itself may influence the activity, specificity etc. of the protein product. In general, one can expect that a short tag of two or three amino acids has no or just a minor effect on folding of the protein (and thereby) the activity, specificity, etc. But there is probably no general rule for this, it depends on the nature of the protein/enzyme.

In another preferred embodiment, the tag may be a modified *Bacillus* SsrA tag. In an especially preferred embodiment the modified tag has the sequence. AGKTNSFNQNVALDD (SEQ ID NO:2) or AGKTNSFNQNVALKK (SEQ ID NO:4).

Isolated or Purified

The terms "isolated" or "purified" as used herein refer to a nucleic acid or amino acid that is removed from at least one component with which it is naturally associated.

Native Protein or Polypeptide

As used herein, the terms "Native protein" or "Native polypeptide" are used interchangeably herein and refer to a protein or polypeptide which has not been modified or altered at the last two amino acid residues located at the carboxy-terminus. In other words, the last two amino acid residues at the carboxy-terminus of the expressed protein or polypeptide are the same as those found in the naturally occurring protein or polypeptide. Other residues within the protein or polypeptide may be altered, modified or mutated.

Heterologous Protein

As used herein, the term "heterologous protein" refers to a protein or polypeptide that does not naturally occur in a host cell. Examples of heterologous proteins include enzymes such as hydrolases including proteases, cellulases, amylases, other carbohydrases, and lipases; isomerases such as racemases, epimerases, tautomerases, or mutases; transferases, kinases and phophatases, hormones, growth factors, cytokines, antibodies and the like.

Homologous Protein

The term "homologous protein" refers to a protein or polypeptide native or naturally occurring in a host cell. The invention includes host cells producing the homologous protein via recombinant DNA technology. The present invention encompasses a host cell having a deletion or interruption of the nucleic acid encoding the naturally occurring homologous protein, such as a protease, and having nucleic acid encoding the homologous protein re-introduced in a recombinant form. In another embodiment, the host cell produces the homologous protein.

Nucleic Acid Molecule

The term "nucleic acid molecule" includes RNA, DNA and cDNA molecules. It will be understood that, as a result of the degeneracy of the genetic code, a multitude of nucleotide sequences encoding a given protein may be produced. The present invention contemplates every possible variant nucleotide sequence, encoding tag sequences, including but not limited to the individual amino acid residues of D, E, K and N, all of which are possible given the degeneracy of the genetic code.

A "heterologous" nucleic acid construct or sequence has a portion of the sequence that is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native cell.

Vector

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Expression Cassette

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

Plasmid

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in mammalian cells and where expression of the selectable marker confers to cells containing the expressed gene the ability to grow in the presence of a corresponding selective agent.

Promoter

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed cells. A typical chimeric gene of the present invention, for transformation into a host cell, includes a transcriptional regulatory region that is constitutive or inducible, a signal peptide coding sequence, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader, i.e., a signal peptide, is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

The gene may encode therapeutically significant proteins or peptides, such as growth factors, cytokines, ligands, receptors and inhibitors, as well as vaccines and antibodies. The gene may encode commercially important industrial proteins or peptides, such as enzymes, e.g., proteases, carbohydrases such as amylases and glucoamylases, cellulases, oxidases and lipases. The gene of interest may be a naturally occurring gene, a mutated gene or a synthetic gene.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5–10° below the Tm; "intermediate stringency" at about 10–20° below the Tm of the probe; and "low stringency" at about 20–25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5× Denhardt's solution, 0.5% SDS and 100 $\mu$g/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a non-native (heterologous) nucleic acid sequence integrated into its genome or as an episomal plasmid that is maintained through two or more generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

Proteolysis in bacteria serves to rid the cell of abnormal and misfolded proteins. A unique mechanism for the destruction of abnormal proteins resulting from abortive termination of translation is provided by the SsrA-mediated tagging and degradation system (for a recent review, see Karzai et al. 2000. The SsrA-SmpB system for protein tagging, directed degradation and ribosome rescue. Nat. Struct. Biol. 7:449–455). SsrA, also called 10Sa RNA or tmRNA is a highly conserved RNA molecule in eubacteria. It is a unique molecule that can act as both a tRNA and an mRNA in a process referred to as trans-translation (Atkins et al. 1996. A case for trans translation. Nature 379:769–771; Jentsch 1996. When proteins receive deadly messages at birth. Science 271:955–956; Keiler et al. 1996. Role of a peptide tagging system in degradation of proteins synthesized from damaged messenger RNA. Science 271:990–993). This mechanism provides the cell a way to release ribosomes that are stalled on untranslatable mRNAs, e.g. mRNAs lacking in-frame stop codons. In the model for SsrA action, SsrA charged with alanine enters the A site of a stalled ribosome, mimicking a tRNA. The alanine is added to the uncompleted polypeptide chain; and then, serving as an mRNA, SsrA provides a short reading frame followed by a stop codon as a template to add a short peptide to the nascent polypeptide before translation terminates and a tagged protein is released. The peptide tag (encoded by SsrA) functions as a proteolytic degradation signal, and in *Escherichia coli* four proteases have been identified that degrade proteins tagged by SsrA. ClpXP, ClpAP, and FtsH (HflB) degrade SsrA tagged proteins in the cytoplasm (Gottesman et al. 1998. The ClpXP and ClpAP proteases degrade proteins with carboxy-terminal peptide tails added by the SsrA-tagging system. Genes Dev. 12:1338–1347; Herman et al. 1998. Degradation of carboxy-terminal-tagged cytoplasmic proteins by the *Escherichia coli* protease HflB (FtsH). Genes Dev. 12:1348–1355), while SsrA tagged proteins with signal peptides that are exported to the periplasm of *E. coli* are degraded by Tsp (Prc) protease (Keiler et al. 1996).

Not only ribosome stalling on messages without in-frame stop codons leads to activation of the SsrA tagging system. It also occurs when ribosomes stall at clusters of rare codons in an mRNA when the cognate tRNA is scarce (Roche et al. 1999. SsrA-mediated peptide tagging caused by rare codons and tRNA scarcity. EMBO J. 18:4579–4589), and there may be more conditions that result in SsrA tagging. The whole story leading to the elucidation of SsrA function started with the observation by Tu et al. (1995. C-terminal extension of truncated recombinant proteins in *Escherichia coli* with a 10Sa RNA decapeptide. J. Biol. Chem. 270:9322–9326) that a fraction of mouse interleukin-6 expressed in *E. coli* is truncated and contained the SsrA tag. It is not clear why in this case part of the mIL-6 molecules were tagged by SsrA. Perhaps mIL-6 mRNA is relatively unstable in *E. coli*, leading to transcripts that are trimmed at the 3' end by nucleases, thereby losing its stop codon. Alternatively, mIL-6 overexpression itself may lead to jamming at the ribosomes, thereby activating the SsrA tagging system. Whatever the reason is, contamination of recombinant proteins with molecules that are truncated and tagged by the SsrA system (and escape from degradation) restricts the usefulness of these molecules e.g. as pharmaceutical proteins. Therefore, peptide tagging according to the present invention, i.e., the utilization of a charged tag, in *B. subtilis*, an industrially important species used for the commercial production of various proteins provides a substantial benefit not found in the prior art.

*B. subtilis* SsrA has been isolated and sequenced several years ago (Ushida et al. 1994 tRNA-like structures in 10Sa RNAs of *Mycoplasma capricalum* and *Bacillus subtilis*. Nucleic Acids Res. 22:3392–3396) and the sequence of the proteolysis tag encoded by *B. subtilis* SsrA ((A) GKTNSFNQNVALAA SEQ ID NO:1) has been predicted (Williams 2000. The tmRNA website. Nucleic Acids Res. 27:165–166). Recently, Wiegert and Schumann (2001. SsrA-mediated tagging in *Bacillus subtilis*. J. Bacteriol. 183:3885–3889) showed that the ClpXP protease is responsible for the degradation of intracellular SsrA-tagged proteins in *B. subtilis*. The instant invention provides for an enhanced protein stability via enhance protease resistance. In particular, the extracellular protease CtpA, and perhaps one or more of the major extracellular proteases of *B. subtilis*, play a role in the degradation of an extracellular, heterologous protein that was tagged by the SsrA system. It is a benefit that tagged proteins according to the present invention are more resistant to proteolysis.

Possible Signal Sequences that may be Used

It is contemplated that any signal sequence that directs the nascent polypeptide into a secretory pathway may be used in the present invention. It is to be understood that as new signal sequences are discovered that they will be encompassed by the invention.

Signal peptides from two secretory pathways are specifically contemplated by the instant invention. The first pathway is the sec-dependent pathway. This pathway is well characterized and a number of putative signal sequences have been described. It is intended that all sec-dependent signal peptides are to be encompassed by the present invention. Specific examples include but are not limited to the AmyL and the AprE sequences. The AmyL sequence refers to the signal sequence for α-amylase and AprE refers to the AprE signal peptide sequence [AprE is subtilisin (also called alkaline protease) of *B. subtilis*].

The second pathway is the twin arginine translocation or Tat pathway. Similarly, it is intended that all tat-dependent signal peptides are to be encompassed by the present invention. Specific examples include but are not limited to the phoD and the lipA sequences.

Possible Proteins that may be Produced

The present invention is particularly useful in enhancing the production and secretion of proteins that possess non-polar or substantially non-polar carboxy termini. Thus, it is contemplated that a protein that comprises a signal sequence and a non-polar or substantially non-polar carboxy terminus would be useful in the present invention. The protein may be homologous or heterologous. Proteins that may produced by the instant invention include, but are not limited to, hormones, enzymes, growth factors, cytokines, antibodies and the like.

Enzymes include, but are not limited to, hydrolases, such as protease, esterase, lipase, phenol oxidase, permease, amylase, pullulanase, cellulase, glucose isomerase, laccase and protein disulfide isomerase.

Hormones include, but are not limited to, follicle-stimulating hormone, luteinizing hormone, corticotropin-releasing factor, somatostatin, gonadotropin hormone, vasopressin, oxytocin, erythropoietin, insulin and the like.

Growth factors are proteins that bind to receptors on the cell surface, with the primary result of activating cellular proliferation and/or differentiation. Growth factors include, but are not limited to, platelet-derived growth factor, epidermal growth factor, nerve growth factor, fibroblast growth factors, insulin-like growth factors, transforming growth factors and the like.

Cytokines are a unique family of growth factors. Secreted primarily from leukocytes, cytokines stimulate both the humoral and cellular immune responses, as well as the activation of phagocytic cells. Cytokines include, but are not limited to, colony stimulating factors, the interleukins (IL-1 (α and β), IL-2 through IL-13) and the interferons (α, β and γ).

Human Interleukin-3 (IL-3) is a 15 kDa protein containing 133 amino acid residues. IL-3 is a species specific colony stimulating factor which stimulates colony formation of megakaryocytes, neutrophils, and macro phages from bone marrow cultures.

Antibodies include, but are not limited to, immunoglobulins from any species from which it is desirable to produce large quantities. It is especially preferred that the antibodies are human antibodies. Immunoglobulins may be from any class, i.e., G, A, M, E or D.

Possible Tags that may be Used

Tags may either be added to the carboxy terminus of a protein or substituted for the amino acids of the protein's carboxy terminus. If the protein has been tagged by the addition of amino acid residues the tag is preferably up to 20 additional residues preferably about. 15, more preferred 1–14, even more preferred 1–11, and most preferred 1–3, wherein the last one or two amino acid residues are charged. FIG. 7D depicts a protein with a tag added on to its carboxy terminus (SEQ ID NO:28). In this depiction the tag is 14 amino acid residues long.

In the alternative, the tag may replace between 1 and 5 amino acids in the protein's carboxy terminus. In the substituted tag the amino acids are charged. In a preferred embodiment the last 5 amino acids are replaced with the tag. In another preferred embodiment the last 4 amino acids are replaced with the tag. In yet another preferred embodiment the last 3 amino acids are replaced with the tag. In a more preferred embodiment the last amino acid is replaced with the tag. In a most preferred embodiment the last 2 amino acids are replaced with the tag. FIG. 7C depicts a substitution tagged protein (SEQ ID NO:27). In this depiction the final two amino acid residues of the native protein have been replaced with two charged amino acid residues.

The charged amino acid residues may be either positively or negatively charged. The preferred negatively charged amino acids are: D or E. The preferred positively charged amino acids are: K, R or H.

The following preparations and examples are given to enable those skilled in the art to more clearly understand and practice the present invention. They should not be considered as limiting the scope and/or spirit of the invention, but merely as being illustrative and representative thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); Ci (Curies) mCi (milliCuries); μCi (microCuries); TLC (thin layer achromatography); SDS-PAGE (Sodium dodecylsulfate polyacrylamide gel electophoresis); Ts (tosyl); Bn (benzyl); Ph (phenyl); Ms (mesyl); Et (ethyl), Me (methyl).

EXAMPLE 1

Plasmid Construction and Host Transformation

To study the degradation of SsrA-tagged proteins in *B. subtilis*, variants of pLATIL3 were made in which h-IL3 is expressed with different short peptide tags added to the COOH-terminus of h-IL3:

Variant 1: plasmid pLATIL3-BStag; expresses the hIL3 variant hIL3-AA: hIL3 with an apolar C-terminal *B. subtilis* SsrA-tag [GKTNSFNQNVALAA] (SEQ ID NO:5)

Variant 2: plasmid pLATIL3-DDtag; expresses the hIL3 variant hIL3-DD: hIL3 with a negatively charged C-terminal tag [GKTNSFNQNVALDD] (SEQ ID NO:6), this variant differs from variant 1 (hIL3-AA) only in the last two C-terminal amino acids (two aspartic acids (DD) instead of two alanine (AA) residues)

Variant 3: plasmid pLATIL3-ECtag; expresses the hIL3 variant hIL3-ECAA: hIL3 with an apolar C-terminal *E. coil* SsrA tag [AANDENYALAA] (SEQ ID NO:3).

Plasmids, bacterial strains and media. Table I lists the plasmids and bacterial strains used in this study. *E. coli* strains were grown in or on 2×YT medium (Bacto tryptone, 16 g/l; yeast extract, 10 g/l; and NaCl, 5 g/l). *B. subtilis* strains were grown in TSB (Tryptone Soya Broth from Oxoid, 30 g/l), or 2×SSM (Spizizen's minimal medium; Harwood et al. 1990 Molecular biological methods for *Bacillus*. John Wiley and Sons, Chichester, United Kingdom), or on SMA (Spizizen's minimal agar; Harwood et al. 1990), or HI-agar (Heart Infusion agar from Difco, 40 g/l). When appropriate, media were supplemented with ampicillin, 100 μg/ml; chloramphenicol, 5 μg/ml; erythromycin, 1 μg/ml; neomycin, 10 μg/ml; spectinomycin, 100 μg/ml; tetracycline, 10 μg/ml and/or isopropyl-β-D-thiogalactopyranoside (IPTG; 500 μM).

Plasmid DNA was isolated with the QIAprep spin mini-prep kit (Qiagen) according to the instructions, except that *B. subtilis* cells were incubated with lysozyme (5 mg/ml in buffer P1) for 10' at 37° C. prior to addition of lysis buffer (buffer P2). Chromosomal DNA was isolated as described previously (Harwood et al. 1990). Procedures for DNA restriction, ligation, agarose gel electrophoresis, and transformation of *E. coli* were carried out as described in Sambrook et al. (1989. Molecular Cloning: A laboratory manual, 2nd ed. Cold Spring Harbor Laboratory Press, Cold Spring Harbor, N.Y.). Enzymes were from Life technologies.

Transformation of competent cells was used to transfer DNA (plasmids, linear DNA) into *B. subtilis* (Harwood et al. 1990). PCR (polymerase chain reaction) was carried out with High Fidelity Platinum Taq DNA Polymerase (Life technologies) and if required PCR fragments were purified with the Qiaquick PCR purification kit (Qiagen). DNA primers were from Life technologies and DNA sequencing was performed by BaseClear (Leiden, The Netherlands). Plasmid pLATIL3TERM was obtained by PCR on pLATIL3 with the primers pLATIL3SXHfw (5' GTC GAC CTC GAG ACC CCA AGC TTG GCG TAA TC 3') (SEQ ID NO:7) and pLATIL3T3rv (5' GTC GAC CTC GAG CGG GAG AAT CTT TTT TTG ATT CTG CCG CAA AGT CGT CTG TTG AGC CTG 3') (SEQ ID NO:8). The resulting DNA fragment was purified, digested with XhoI, self-ligated, and transformed directly into *B. subtilis*. One of the plasmid clones, found to be correct by DNA sequencing, was designated pLATIL3TERM. This plasmid holds the transcription terminator of the folC gene (present in primer pLATIL3T3rv) at the 3' end of the AmyL-hIL-3 gene, just in front of an in-frame stop codon. Plasmid pLATILBStag was obtained by a PCR on pLATIL3 with the primers pLATIL3T2FW (5' CTG CAG CTC GAG GAT ATC GTC GAC CGG CAG AAT CAA AAA AAG ATT CTG CCG ACC CCA AGC TTG GCG TAA TC 3') (SEQ ID NO:9) and pIL3BStagRV (5' CTT CTA CTC GAG TCA GGC AGC TAA TGC TAC GTT TTG GTT AAA ACT GTT AGT TTT GCC TGC GCT CAA AGT CGT CTG TTG AGC 3') (SEQ ID NO:10). The resulting PCR fragment was purified, digested with Xhol, self-ligated, and transformed into *B. subtilis*. A few clones were checked by DNA sequencing and one correct clone was selected and named pLATIL3BStag. Plasmid pLATIL3DDtag and pLATIL3ECtag were made in the same way but instead of primer pIL3BstagRV, primer pIL3DDtagRV (5' CTT CTA CTC GAG TCA GTC GTC TAA TGC TAC GTT TTG GTT AAA ACT GTT AGT TTT GCC TGC GCT CPA AGT CGT CTG TTG AGC 3') (SEQ ID NO:11) and primer pIL3EctagRV (5' CTT CTA CTC GAG TCA AGC TGC TAA AGC GTA GTT TTC GTC GTT TGC TGC GCT CAA AGT CGT CTG TTG AGC 3') (SEQ ID NO:12) were used, respectively. To construct *B. subtilis* ΔssrA mutants, ssrA and its flanking regions (approximately 2.2 kb) was amplified by PCR With the primers pSsrAFW (5' CAG CTC CGT CTG AGG AAA AAG 3') (SEQ ID NO:13) and pSsrARV (5' CGA AGT GGG CGA TTT CTT CCG 3') (SEQ ID NO:14) and cloned into pCR2.1-TOPO, resulting in plasmid pTPSsrA. Plasmid pSsrASp was obtained by inserting a pDG1726-derived Sp resistance marker (Guérout-Fluery et al. 1995. Antibiotic-resistance cassettes for *Bacillus subtilis*. Gene 167:335–336) into the unique Sad site in the ssrA gene of pTPSsrA. Finally, *B. subtilis* 168 ΔssrA and WB600 ΔssrA were obtained by a double cross-over recombination event between the disrupted ssrA gene of pSsrASp and the chromosomal ssrA gene in *B. subtilis* 168 and WB600, respectively. $SsrA^{DD}$ expressing *B. subtilis* strains were made as follows: a fragment consisting of a 5' end part of ssrA including the ssrA promoter region, was amplified with the primers pSsrAHindeIIIfw (5' TTC TAA AAG CTT AGT GCT TGA TTC GAA AAT CAG GCC TGT G 3') (SEQ ID NO:15 and pSsrADDintRV (5' GAG CTC GCT GCG CTT ATT AGT CGT CTA ATG CTA CGT TTT GGT TAA 3') (SEQ ID NO:16); contains the alteration of the two alanine codons in the SsrA tag sequence into codons for aspartic acid residues). In addition, an overlapping 3' end part of ssrA was amplified with the primers pSSrADDintFW (5' TTA ACC AAA ACG TAG CAT TAG ACG ACT AAT AAG CGC AGC GAG CTC 3') (SEQ ID NO: 17); also containing the alteration of the two alanine codons into codons for two aspartic acid residues) and pSsrASphIRV (5' CCT CCG TGC ATG CTT CCT CTT ATT TAT TGA CAG AAA TCT G 3') (SEQ ID NO:18). Both fragments were assembled in a fusion PCR with primers pSsrAHindIIIFW and pSsrASphIRV, and cloned in pCR2.1-TOPO, resulting in plasmid pSsrADD. The correct sequence of the fusion product in pSsrADD was confirmed by DNA sequencing. Next, a selective marker (the Tc resistance cassette derived from pDG 1515; Guérout-Fluery et al. 1995. Antibiotic-resistance cassettes for *Bacillus subtilis*. Gene 167:335–336) that functions in *B. subtilis*, was cloned into the EcoRV site of pSsrADD, resulting in plasmid pSsrADDTc. Finally, *B. subtilis* 168 $IssrA^{DD}$ and WB600 $IssrA^{DD}$ were obtained by a Campbell-type integration (single cross-over) of pSsrADDTc into one of the disrupted ssrA regions on the chromosome of *B. subtilis* 168 ΔssrA and WB600 ΔssrA, respectively. These strains contain an active copy of the $ssrA^{DD}$ gene on the chromosome (under control of the native ssrA promoter) and a disrupted copy of wild-type ssrA (insertion of the Sp resistance marker), as confirmed by POR. To construct *B. subtilis* WB600 ΔctpA, WB600 was transformed with chromosomal DNA of BSE-23. In BSE-23, the ctpA gene is replaced by a spectinomycin resistance cassette (Edwin Lee, Genencor International Palo Alto, unpublished). WB600 ΔyvjB was obtained as follows: yvjB and its flanking regions (approximately 3.5 kb) was amplified by PCR with the primers pYvjBFW (5' AGA GTT TTA AAT CTC TCG GGA GAA ACA CAT GGA TGA CAT T 3') (SEQ ID NO:19) and pYvjBRV (5' TGT ATA TGT AAA TTT CAG ATC ATC ATA AAT ATC TGC TAT T 3') (SEQ ID NO:20) and cloned in pCR2.1-TOPO, resulting in plasmid pTPYvjB. Plasmid pTPYvjBTc was obtained by replacing an internal SmaI-AccI fragment of the yvjB gene in pTPYvjB with a pDG 1515-derived Tc resistance marker (Guérout-Fluery et al. 1995. Antibiotic-resistance cassettes for *Bacillus subtilis*. Gene 167:335–336) Finally, *B. subtilis* WB600 ΔyvjB was obtained by a double cross-over recombination event between the disrupted yvjB gene of pTPYvjBTc and the chromosomal yvjB gene. To construct *B. subtilis* WB600 lclpP, the 5' end region of the cIpP gene was amplified by POR with the primers pCIpPEcoFW (5' CTT ACC GAA TTC GTG AAG GAG GAG CAT TAT G 3') (SEQ ID NO:21) containing a EcoRI site, and pClpPBamRV (5' GCC TTT GGA TCC GGC TGC AAG CAG GAA CGC 3') (SEQ ID NO:22) containing a BamHI site. The amplified fragment was cleaved with EcoRI and BamHI, and cloned in the corresponding sites of pMutin2 (Vagner et at. 1998. A vector for systematic gene inactivation in *Bacillus subtilis*. Microbiology 144:3097–3104), resulting in plasmid pMutClpP. *B. subtilis* WB600 IcIpP was obtained by a Campbell-type integration (single cross-over) of pMutClpP into the cIpP region on the chromosome. Cells of this strain are depleted for CIpP by growing them in medium without IPTG (Vagner et at. 1998).

TABLE 1

Plasmids and Strains

| Plasmid/Strain | Properties | Reference |
|---|---|---|
| pLATIL3 | derivative of pGB/IL-322: contains the human IL-3 gene fused to the sequence encoding the signal peptide of *B. licheniformis* α-amylase (amyL-hIL-3); the amyL-hIL-3 gene fusion is under control of the amylase promoter; 4.3 kb; $Nm^R$ | Van Leen et al. 1991 Production of human interleukin-3 using industrial microorganisms. Biotechnology 9:47–52. |
| pLATIL3TERM | derivative of pLATIL3; contains the transcription terminator of the *B. subtilis* folC gene inserted just in front of the stop codon of amyL-hIL-3; 4.1 kb; $Nm^R$ | This work |
| pLATIL3BStag | derivative of pLATIL3; contains amyL-hIL-3 fused at the 3'end to the sequence encoding the *B. subtilis* SsrA peptide tag (AGKTNSFNQNVALAA SEQ ID NO:1); 4.2 kb; $Nm^R$ | This work |
| pLATIL3DDtag | derivative of pLATIL3; contains amyL-hIL-3 fused at the 3'end to the sequence encoding a variant SsrA-DD-tag (AGKTNSFNQNVALDD SEQ ID NO:2); 4.2 kb; $Nm^R$ | This work |
| pLATIL3ECtag | derivative of pLATIL3; contains amyL-hIL-3 fused at the 3'end to the sequence encoding the *E. coli* SsrA peptide tag (AANDENYALAA SEQ ID NO:3); 4.2 kb; $Nm^R$ | This work |
| pCR2.1-TOPO | TA cloning vector for PCR products; 3.9 kb; $Ap^R$; $Km^R$ | Invitrogen |
| pTPSsrA | pCR2.1-TOPO derivative; carrying the ssrA gene + flanking regions; 6.1 kb; $Ap^R$; $Km^R$ | This work |

TABLE 1-continued

Plasmids and Strains

| Plasmid/Strain | Properties | Reference |
|---|---|---|
| pSsrASp | derivative of pTPSsrA for the disruption of ssrA; 7.0 kb; $Ap^R$; $Km^R$; $Sp^R$ | This work |
| pSsrADD | pCR2.1-TOPO derivative; carrying a $ssrA^{DD}$ gene variant: the last two codons of the tag sequence in ssrA (gct gcc) encoding two alanines are changed into gac gac, encoding two aspartic acid residues; 4.6 kb; $Ap^R$; $Km^R$ | This work |
| pSsrADDTc | derivative of pSsrADD; carrying $ssrA^{DD}$ and a Tc resistance cassette; for integration of $ssrA^{DD}$ on the *B. subtilis* chromosome; 6.8 kb; $Ap^R$; $Km^R$; $Tc^R$ | This work |
| pTPYvjB | pCR2.1-TOPO derivative; carrying the yvjB gene + flanking regions; 7.4 kb; $Ap^R$; $Km^R$ | This work |
| pTPYvjBTc | derivative of pTPYvjB for the disruption of yvjB; 8.9 kb; $Ap^R$; $Km^R$; $Tc^R$ | This work |
| pMutin2 | pBR322-based integration vector for *B. subtilis*; containing a multiple cloning site downstream of the Pspac promoter, and a promoter-less 1998 lacZ gene preceded by the RBS of the spoVG gene; 8.6 kb; $Ap^R$; $Em^R$ | Vagner et al. 1998. A vector for systematic gene inactivation in *Bacillus subtilis*. Microbiology 144:3097–3104. |
| pMutClpP | pMutin2 derivative; carrying the 5' part of the *B. subtilis* clpP gene; 8.9 kb; $Ap^R$; $Em^R$ | This work |
| Strains | | |
| *E. coli* | | |
| TOP10 | F mcrA Δ(mrr-hsdRMS-mcrBC) Φ80lacZΔM15 ΔlacX74 recA1 deoR araD139 Δ(ara-leu)7697 galU galK rpsL ($Str^R$) endA1 nupG | Invitrogen |
| XL1-Blue | recA1 endA1 gyrA96 thi-1 hsdR17 supE44 relA1 lac [F¢proAB $lacI^qZDM15$ Tn10 ($Tet^r$)] | Stratagene |
| *B. subtilis* | | |
| 168 | trpC2 | Kunst et al. 1997. The complete genome sequence of the Gram-positive bacterium *Bacillus subtilis*. Nature 390:249–256. |
| 168 ΔssrA | trpC2, ssrA ; $Sp^R$ | This work |
| 168 $lssrA^{DD}$ | trpC2, $lssrA^{DD}$; $Tc^R$; integration of pSsrADDTc in ssrA::spec in 168 ΔssrA | This work |
| WB600 | trpC, nprE, aprE, epr, bpf, mpr, nprB | Wu et al. 1991. Engineering a *Bacillus subtilis* expression-secretion system with a strain deficient in six extracellular proteases. J. Bacterial. 173:4952–4958. |
| BSE-23 | ctpA; $Sp^R$ | E. Lee, unpublished |
| WB600 ΔctpA | trpC, nprE, aprE, epr, bpf, mpr, nprB, ctpA; $Sp^R$ | This work |

TABLE 1-continued

| Plasmids and Strains | | |
|---|---|---|
| Plasmid/Strain | Properties | Reference |
| WB600 ΔyvjB | trpC, nprE, aprE, epr, bpf, mpr, nprB yvjB; $Tc^R$ | This work |
| WB600 lclpP | trpC, nprE, aprE, epr, bpf, mpr, nprB, Pspac-clpP; clpP-lacZ; $Em^R$ | This work |
| WB600 ΔssrA | trpC, nprE, aprE, epr, bpf, mpr, nprB, ssrA; $Sp^R$ | This work |
| WB600 $lssrA^{DD}$ | trpC, nprE, aprE, epr, bpf, mpr, nprB, $lssrA^{DD}$; $Tc^R$ | This work |

EXAMPLE 2

IL-3 Expression

When fused to the signal peptide of *B. licheniformis* α-amylase, human interleukin-3 can be secreted by *B. subtilis* (Van Leen et al. (1991), Biotechnology, 9: 47–52). Plasmid pLATIL3 contains the h-IL3 gene fused to the coding region of the *B. licheniformis* α-amylase (AmyL) signal peptide; in this plasmid expression of the hybrid AmyL-hIL3 gene is controlled by the *B. licheniformis* α-amylase promoter. During secretion, the AmyL signal peptide is removed from the AmyL-hIL3 precursor by signal peptidases, and mature hIL3 is released into the medium.

Expression of the human IL-3 gene lacking an in-frame stop codon in wild-type *B. subtilis* and in an ssrA mutant. Mutant 168 ΔssrA was created, in which the ssrA gene is disrupted by insertion of a spectinomycin resistance cassette. The mutation was checked by PCR, and the absence of SsrA RNA in the mutant was confirmed by Northern blot analysis (FIG. 1A). Growth of 168 ΔssrA was somewhat reduced compared to the wild-type strain (FIG. 1B), as reported recently by Muto et al. (2000. Requirement of transfer-messenger RNA for the growth of *Bacillus subtilis* under stresses. Genes Cells 5:627–635). They also observed that growth rates of cells without SsrA decreased with elevating temperatures (>45° C.). In addition, our results show that growth is more affected at low temperatures (<25° C.) then at temperatures between 30–45° C. (FIG. 2C), indicating a mild cold-sensitivity of growth in mutant 168 ΔssrA.

Plasmid pLATIL3, a derivative of pGB/IL-322, contains an expression cassette for the production of human interleukin-3 (hIL-3) by *Bacilli* (Van Leen et al. 1991). In this construct, the *B. licheniformis* α-amylase (AmyL) signal peptide is used to direct secretion of mature hIL-3. As a model for SsrA-mediated peptide tagging in *B. subtilis*, a variant of plasmid pLATIL3 was created in which a transcription terminator is inserted into the AmyL-hIL3 gene, just in front of its stop codon. Transformation of this plasmid (pLATIL3TERM) into *B. subtilis* will result in AmyL-hIL3 transcripts lacking in-frame stop codons. According to the tmRNA model for SsrA mediated tagging of proteins (Keiler et al. 1996), translation of these transcript will result in ribosome stalling, and subsequently recruitment of SsrA, peptide tagging, and finally degradation of the tagged hIL-3 molecules by specific proteases. To test this model in *Bacillus*, the extracellular proteins produced in cultures of *B. subtilis* 168 (pLATIL3TERM), 168 ΔssrA (pLATIL3TERM), and the control strain 168 (pLATIL3), were analyzed by Western blotting (FIG. 2). Human IL-3 accumulated in the medium of strain 168 ΔssrA (pLATIL3TERM), but could not be detected in the medium of *B. subtilis* 168 (pLATIL3TERM) containing functional SsrA. These data indicate that *B. subtilis* SsrA has a role in a process in which proteins translated from mRNAs lacking an in-frame stop codon are degraded. In contrast, in cells without SsrA the hIL-3 molecules are released from stalled ribosomes by an SsrA-independent mechanism (see below). These molecules do not receive a peptide-tag and, therefore are not rapidly degraded by *B. subtilis.*

RNA isolation and Northern blotting. RNA was isolated with the TRIzol method according to the protocol provided by the manufacturer (Life technologies), but with one modification: cells were incubated for 10 min at 37° C. with lysozyme (2 mg/ml) prior to lysis in TRIzol solution. Northern blotting was performed after electrophoresis of RNA through gels containing formaldehyde (Sambrook et al. 1989). To this purpose, Hybond-N+nylon membrane from Amersham Pharmacia Biotech was used. The SsrA-specific probe was amplified by PCR with the primers SsrAFRWDP (5' ACG TTA CGG ATT CGA CAG GGA TGG 3') (SEQ ID NO:23) and SsrAREVP (5' GAG TCG AAC CCA CGT CCA GAA A 3') (SEQ ID NO:24). Labeling of the probe, hybridization and detection was performed with the ECL direct nucleic acid labeling and detection system from Amersham Pharmacia Biotech according to the manufacturer's instructions.

EXAMPLE 3

Enhanced Protease Resistance

A pulse-chase assay was performed with the strains *B. subtilis* 168 (pLATIL3-BStag) and *B. subtilis* 168 (pLATIL3-DDtag) (FIG. 2). NB: the h-IL3 variants expressed by these two strains (hIL3-AA and hIL3-DD) differ only in the last two COOH-terminal amino acids: two alanine residues in hIL3-AA and two aspartic acid residues for hIL3-DD. In the pulse-chase experiment, the initial level (pulse 1 min; chase 0') of extracellular hIL3-DD proved to be roughly 5 times higher than that of hIL3-AA (compare lane 1 with lane 7). In addition, hIL3-AA proteins were degraded with half lives of <2 min, while the h-IL3-DD molecules had half-lives of approximately 5 min.

Protein labeling, SDS-PAGE, and fluorography. Pulse-chase labeling of *B. subtilis* and SDS-PAGE was essentially as described previously (Van Dijl et al. 1991. Non-functional expression of *Escherichia coli* signal peptidase I in *Bacillus subtilis*. J. Gen. Microbiol. 137:2073–2083). However, samples collected after chase times of 0, 5, 10, 30, and 60 min were centrifuged for 10 seconds, and only the extracellular proteins (in the culture supernatant) were precipitated with trichloroacetic acid (TCA) and eventually subjected to SDS-PAGE. Fluorography was performed with Amplify fluorographic reagent (Amersham-Pharmacia Biotech). Protein bands were quantified using the Storm PhosphorImager system (Molecular Dynamics).

Western blot analysis. To obtain anti-BsSsrAtag antibodies (antibodies that recognize proteins with a C-terminal *B. subtilis* SsrA-tag), synthetic peptide AGKTNSFNQNVA-LAA (SEQ ID NO:1) (coupled via an amino-terminal cysteine residue to KLH carrier) was injected into rabbits (Eurogentec). Serum of the final bleed of one of the rabbits was selected for affinity purification, and this purified serum was used in the Western blot procedures. Antibodies against human IL-3 were mouse monoclonals (Van Leen et al. 1991. Production of human interleukin-3 using industrial microorganisms. Biotechnology 9:47–52). Immunoblotting and detection was performed with alkaline phosphatase-labeled conjugate and the BM Chromogenic Western Blotting kit (Roche Diagnostics) according to the instructions of the manufacturer.

Stability of hIL-3 variants with different C-terminal tags produced by *B. subtilis*. To further investigate whether the *B. subtilis* SsrA tag functions as a degradation signal for secreted proteins, three variants of plasmid pLATIL3 were created. Plasmid pLATIL3BStag contains a gene variant encoding hIL-3 fused at the C-terminus to the *B. subtilis* SsrA peptide tag (AGKTNSFNQNVALAA SEQ ID NO:1), plasmid pLATIL3ECtag contains a gene variant encoding h-IL3 fused at the C-terminus to the *E. coli* SsrA tag (AANDENYALAA SEQ ID NO:3). The third plasmid pLATIL3DDtag contains a gene encoding h-IL3 fused at the C-terminus to the sequence encoding a DD-tag (AGKTNSFNQNVALDD SEQ ID NO:2). This tag is equal to the *B. subtilis* SsrA-tag (AA-tag), but instead of two alanines at the extreme C-terminus it contains two aspartic acid residues. The DD-tag was suspected to be relatively resistant to proteolytic degradation, as observed for *E. coil* (Abo et al. 2000. SsrA-mediated tagging and proteolysis of Lacl and its role in the regulation of lac operon. EMBO J. 19:3762–3769; Roche et al. 1999). The extracellular proteins produced by cells of *B. subtilis* 168 containing pLATIL3, pLATIL3BStag, pLATIL3DDtag, or pLATIL3ECtag, were analyzed by Western blotting (FIG. 3A). The amount of the hIL-3-DDtag present in the medium was found to be roughly 5 times higher then that of wild-type hIL-3, hIL-3-AAtag or hIL-3-ECtag. Human interleukin-3 molecules produced by wild-type *B. subtilis* are relatively unstable due to proteolytic degradation, and the results represented in FIG. 3A suggest that addition of a C-terminal SsrA-tag does not lead to increased degradation of hIL-3 molecules. It is important to note, however, that in *E. coli* proteins tagged cotranslationally by the SsrA system are degraded more rapidly than proteins with essentially the same sequence in which the SsrA tag is DNA encoded (Gottesman et al. 1998. The ClpXP and CIpAP proteases degrade proteins with carboxy-terminal peptide tails added by the SsrA-tagging system. Genes Dev. 12:1338–1347). The results obtained with pLATIL3TERM (FIG. 2) indicate that this is also true for *B. subtilis*. Strikingly, addition of the DD-tag (with two charged, polar residues at the extreme C-terminus) leads to a higher level of extracellular hIL-3, indicating that DD-tagged hIL-3 is less susceptible to proteolytic degradation. To explore this further, a pulse-chase assay was performed with the *B. subtilis* strain 168 (pLATIL3BStag) and 168 (pLATIL300tag) (FIG. 3B and 3C). The initial level (chase time=0 mm) of hIL-3-DDtag in the medium is approximately 4 times higher then that of hIL-3-AAtag. In addition, the hIL-3-AAtag variant was degraded with a half-life of <2 mm, whereas the half-life of hIL-3-DDtag was somewhat increased (approximately 5 mm). The latter observation supports that DD-tagged hIL-3 is less susceptible to extracellular proteases compared to hIL-3with an AA-tag. However, the observation that the initial level of hIL3-DDtag in the medium is considerably higher then that of hIL3-AAtag indicates that hIL3-AAtag is also subject to proteolytic degradation before the molecules reach the medium, e.g. during passage of the cell wall of *B. subtilis*.

EXAMPLE 4

Prolonged Half-life

Detection of cotranslationally SsrA-tagged hIL-3 secreted by WB600 and by cells expressing an $SsrA^{DD}$ variant. To detect SsrA-tagged h-1L3 molecules secreted by *B. subtilis* and to identify proteases that have a role in the degradation of SsrA-tagged hIL-3, two different approaches were used. First, pLATIL3TERM was expressed in WB600, a *B. subtilis* strain lacking six extracellular proteases (Wu et al. 1991. Engineering a *Bacillus subtilis* expression-secretion system with a strain deficient in six extracellular proteases. J. Bacteriol. 173:4952–4958), which may be responsible for the degradation of extracellular, SsrA-tagged hIL-3. In the medium of a culture of WB600 (pLATIL3TERM), a band was detected reacting with antibodies against hIL-3 as well as with antibodies raised against the predicted *B. subtilis* SsrA-tag (FIG. 4, lane 3 and 8). This band is absent in the medium of *B. subtilis* 168 (pLATIL3TERM) (lanes 2 and 7) and WB600 ΔssrA (pLATIL3TERM) (lanes 4 and 9). Thus, hIL-3 molecules translated from mRNAs that lack termination codons are tagged by *B. subtilis* SsrA. The fact that these tagged molecules react with antibodies raised against the predicted *B. subtilis* SsrA peptide tag (AGKTNSFNQNVALAA SEQ ID NO:1) indicates that this prediction, which was based on comparative sequence analysis of SsrA sequences of several bacteria (Williams 2000), was correct. In addition, it can be concluded that at least one of the major extracellular proteases of *B. subtilis* (those that are absent in WB600) plays a role in the degradation of extracellular, SsrA-tagged h-IL3. When SsrA is absent, stalled ribosomes are released by an SsrA-independent mechanism, referred to as 'run-off translation' (Williams et al. 1999. Resuming translation on tmRNA: a unique mode of determining a reading frame. EMBO J. 18:5423–5433). The upper band in lane 4 probably represents the run-aft translation product of full-length hIL-3 mRNA from pLATIL3TERM, while the bands with lower molecular weight are most likely degradations products thereof. It seems that some run-off translation product is also formed when SsrA is present (lane 3), but it cannot be excluded that this band is just an N-terminal degradation product of SsrA-tagged hIL-3.

As a second approach to detect SsrA-tagged proteins, we constructed *B. subtilis* strains that express an SsrA variant ($SsrA^{DD}$), in which the final two codons of the peptide reading frame are changed to encode aspartic acid residues instead of alanines. As mentioned above, it was shown in *E. coil* that an $Ssr^{ADD}$ variant mediates the addition of a peptide tag that does not lead to rapid degradation (Abo et al. 2000; Karzai et al. 1999. SmpB, a unique RNA-binding protein essential for the peptide-tagging activity of SsrA (tmRNA). EMBO J. 18:3793–3799). Evaluation of the antibodies that were raised against the predicted *B. subtilis* SsrA tag (AGKTNSFNQNVALAA SEQ ID NO:1) showed that they recognize the hIL-3 fused at the C-terminus to either the wild-type tag (AA-tag) or the protease resistant DD-tag (AGKTNSFNQNVALDD SEQ ID NO:2) (data not shown). Human IL-3 molecules tagged by $SsrA^{DD}$ and subsequently secreted (FIG 4, lanes 5 and 10) are indeed relatively more stable then hIL-3 molecules tagged by wild-type SsrA (lanes 3 and 8), even in the six-fold protease negative strain WB600. The level of full-length $SsrA^{DD}$-tagged hIL-3 in the medium is somewhat higher then that of (wild-type) SsrA-tagged h-IL3 (FIG. 3, compare lane 10 with lane 8) and relatively few degradation products of $SsrA^{DD}$-tagged hIL-3 were detected with anti-hIL-3 antibody (compare lane 5 with lane 3). This observation suggests that, besides the major extracellular proteases that are deleted in WB600, one (or more) additional protease is involved in the degradation of SsrA-tagged hIL-3. Therefore, we studied the role of three other proteases with respect to degradation of SsrA-tagged hIL-3.

CtpA has an Additional Role in the Degradation of SsrA-Tagged hIL-3 Secreted by *B. Subtilis.*

Three derivatives of WB600 were constructed. One WB600 ΔctpA, carried a deletion in the ctpA gene, a homologue of the *E. coli* gene encoding Tsp (tail specific protease). The other two, WB600 ΔyvjB and WB600 IclpP, carried a deletion of the yvjB gene (also a homologue of *E. coli* tsp) or the clpP gene placed under control of the IPTG-dependent Pspac promoter of pMutin2, respectively. These three strains, together with WB600 and WB600 ΔssrA, were transformed with plasmid pLATIL3TERM, grown in TSB medium with neomycin, and culture supernatants of cells entering the stationary phase were analyzed by Western blotting with anti-hIL-3 antibodies and anti-Bs-SsrAtag antibodies (FIG. 5). SsrA-tagged h-IL3 could not be detected in the medium of cells lacking SsrA (FIG. 5, lanes 5 and 10), but was present when cells contained functional SsrA (all other lanes). As observed previously (FIG. 3), it seems that some full-length, run-off translation product is not only formed when cells lack SsrA (FIG. 5, lane 5), but also when SsrA is present (lanes 1–4). However, as mentioned before, it cannot be excluded that the protein bands in lanes 1–4, which have the same mobility as full-length, run-off product (upper band in lane 5), represent a degradation product of SsrA-tagged hIL-3. Inactivation of yvjB or clpP in WB600 did not alter the amount of SsrA-tagged hIL-3 in the medium (compare lanes 1 and 6 with lanes 3 and 8, and lanes 4 and 9). The absence of functional CtpA in WB600, however, leads to a higher amount of SsrA-tagged hIL-3 in the medium (lanes 2 and 7) and also to a lower amount of the two smallest degradation products of hIL-3 (lane 2). Thus, the protease CtpA also plays a role in the degradation of SsrA-tagged h-IL3 secreted by *B. subtilis.*

EXAMPLE 5

SsrA Tagging of Native *B. subtilis* Proteins

*B. subtilis* 168 IssrA$^{DD}$ expressing the variant SsrA RNA, containing the protease-resistant DD-tag sequence, was analyzed by Western blotting using the anti-Bs-SsrAtag antibodies to detect native proteins of *B. subtilis* that are tagged through the SsrA system. As controls, cells of *B. subtilis* 168 (expressing wild-type SsrA) and 168 ΔssrA were used. Samples were taken of cells that were in the exponential growth phase or in the stationary phase, and the intracellular proteins and the extracellular proteins were analyzed separately. A large number of intracellular proteins were detected by anti-Bs-SsrAtag antibody when cells expressed SsrA$^{DD}$ (FIG. 6, lanes 2 and 8), while almost all of these bands were absent in cells expressing either wild-type SsrA (lanes 1 and 7) or no SsrA (lanes 3 and 9). As observed in *E. coli* (Abo et al. 2000), these results indicate that many endogenous cellular proteins were tagged by the SsrA system, resulting in chimeric proteins. The proteins with the wild-type SsrA tag (MA-tag) are subsequently degraded by proteases, while proteins with the DD-tag escape from proteolysis. While in the exponential growth phase the majority of the reacting bands were of relatively low molecular weight (lane 2), in the stationary phase a shift was observed towards proteins with a higher molecular weight (lane 8). In the exponential growth phase, no SsrA$^{DD}$-tagged proteins could be detected in the medium (lane 5), while in the stationary phase only a vague smear was observed (lane 11). This is most likely due to cell lysis, by which some intracellular SsrA-tagged proteins end up in the medium. It appears that SsrA-mediated trans-translation occurs quite frequently in normally growing bacilli, and most natural substrates of SsrA seem be to intracellular proteins.

Although the foregoing invention has been described in some detail by way of illustration and example for purposes of clarity and understanding, it will be obvious that certain changes and modifications may be practiced within the scope of the appended claims.

---

What is claimed:

1. A process for enhanced secretion of a polypeptide by bacteria, comprising:

(a) culturing bacterial cells that contain a recombinant expression vector comprising a first DNA sequence encoding a polypeptide that can be secreted by the bacteria and a second DNA sequence encoding a charged, amino-acid tag covalently bonded at the carboxy-terminus of said polypeptide, such that the polypeptide is produced by the cells, and wherein said tag comprises one or two negatively charged amino acid residues; and (b) optionally, recovering the polypeptide from the culture medium.

2. The process of claim 1, wherein said tag comprises two negatively charged amino acid residues or two positively charged amino acid residues.

3. The process of claim 2, wherein said tag comprises two negatively charged amino acid residues, selected from the group consisting of D and E.

4. The process of claim 3, wherein said tag comprises two D residues.

5. The process of claim 2, wherein said tag comprises two positively charged amino acid residues, wherein said two positively charged amino acid residues are lysines (Ks).

6. The process of claim 1, wherein said bacteria is a *Bacillus* species.

7. The process of claim 6, wherein said bacteria is *B. subtilis.*

8. The process of claim 1, wherein said expression vector further includes a DNA sequence encoding a signal peptide operatively linked to said first DNA sequence.

9. The process of claim 8, wherein said signal peptide is *B. licheniformis* α-amylase (AmyL) signal peptide.

10. The process of claim 1, wherein said polypeptide is a heterologous protein selected from the group consisting of hormones, enzymes, and growth factors.

11. The process of claim 10, wherein said protein is human interleukin.

12. A method for enhancing the secretion of a heterologous polypeptide by a *Bacillus species*, comprising: substituting one or more of the C-terminal amino acids residues of said polypeptide with at least one charged amino acid residue, or adding one or more charged amino acid residues to the C-terminus of said polypeptide, wherein the number of amino acid residues substituted or added to the C-terminus of said polypetide comprises two amino add residues.

13. The method of claim 12, wherein the last two amino acid residues of said polypeptide are substituted with a D.

14. The method of claim 12, wherein the last two amino acid residues of said polypeptide are substituted with a E.

15. The method of claim 12, wherein the last two amino acid residues of said polypeptide are substituted with a K.

16. The method of claim 12, wherein two D residues are added at the C-terminus of said polypeptide.

17. The method of claim 12, wherein two E residues are added at the C-terminus of sad polypeptide.

18. The method of claim 12, wherein two K residues are added at the C-terminus of said polypeptide.

* * * * *